US008546124B2

(12) United States Patent
Meulenberg et al.

(10) Patent No.: US 8,546,124 B2
(45) Date of Patent: Oct. 1, 2013

(54) INFECTIOUS CLONES OF RNA VIRUSES AND VACCINES AND DIAGNOSTIC ASSAYS DERIVED THEREOF

(75) Inventors: Johanna Jacoba Maria Meulenberg, Amsterdam (NL); Johannes Maria Antonius Pol, Lelystad (NL); Judy Norma Aletta Bos-de Ruijter, Almere-Buiten (NL)

(73) Assignee: Boehringer Ingelheim Vetmedica GmbH (DE)

( * ) Notice: Subject to any disclaimer, the term of this patent is extended or adjusted under 35 U.S.C. 154(b) by 794 days.

(21) Appl. No.: 11/239,529

(22) Filed: Sep. 29, 2005

(65) Prior Publication Data

US 2006/0205033 A1 Sep. 14, 2006

Related U.S. Application Data

(63) Continuation of application No. 09/874,626, filed on Jun. 5, 2001, now abandoned, which is a continuation of application No. 09/297,535, filed as application No. PCT/NL97/00593 on Oct. 29, 1997, now Pat. No. 6,268,199.

(30) Foreign Application Priority Data

Oct. 30, 1996 (EP) .................................... 96203024

(51) Int. Cl.
*C12N 7/00* (2006.01)

(52) U.S. Cl.
USPC ........................ 435/239; 435/69.1; 435/235.1

(58) Field of Classification Search
USPC ...................................................... 435/235.1
See application file for complete search history.

(56) References Cited

U.S. PATENT DOCUMENTS 3,137,631 A 6/1964 Soloway
3,959,457 A 5/1976 Speaker et al.
4,015,100 A 3/1977 Gnanamuthu et al.
4,122,167 A 10/1978 Buynak et al.
4,205,060 A 5/1980 Monsimer et al.
4,224,412 A 9/1980 Dorofeev et al.
4,452,747 A 6/1984 Gersonde et al.
4,468,346 A 8/1984 Paul et al.
4,554,159 A 11/1985 Roizman et al.
4,606,940 A 8/1986 Frank et al.
4,636,485 A 1/1987 van der Smissen
4,744,933 A 5/1988 Rha et al.
4,753,884 A 6/1988 Kit et al.
4,810,493 A 3/1989 Patrick et al.
4,921,706 A 5/1990 Roberts et al.
4,927,637 A 5/1990 Morano et al.
4,944,948 A 7/1990 Uster et al.
5,008,050 A 4/1991 Cullis et al.
5,009,956 A 4/1991 Baumann
5,132,117 A 7/1992 Speaker et al.
5,206,163 A 4/1993 Renard et al.
5,213,759 A 5/1993 Castberg et al.
5,419,907 A 5/1995 Paul et al.
5,476,778 A 12/1995 Chladek et al.
5,510,258 A 4/1996 Sanderson et al.
5,587,164 A 12/1996 Sanderson et al.
5,597,721 A 1/1997 Brun et al.
5,620,691 A * 4/1997 Wensvoort et al. ........ 424/184.1
5,674,500 A 10/1997 Peeters et al.
5,677,429 A 10/1997 Benfield
5,683,865 A 11/1997 Collins et al.
5,690,940 A 11/1997 Joo
5,695,766 A 12/1997 Paul et al.
5,698,203 A 12/1997 Visser et al.
5,789,388 A 8/1998 Visser et al.
5,840,563 A 11/1998 Chladek et al.
5,846,805 A 12/1998 Collins et al.
5,858,729 A 1/1999 Van Woensel et al.
5,866,401 A 2/1999 Hesse
5,888,513 A 3/1999 Plana Duran et al.
5,910,310 A 6/1999 Heinen et al.
5,925,359 A 7/1999 Van Woensel et al.
5,968,525 A 10/1999 Fitzgerald et al.
5,976,537 A 11/1999 Mengeling et al.
5,989,563 A 11/1999 Chladek et al.

(Continued)

FOREIGN PATENT DOCUMENTS

CA 2103460 A1 12/1992
DD 145705 A1 1/1981

(Continued)

OTHER PUBLICATIONS

Moormann et al. J Virology 1996 vol. 70, No. 2, pp. 763-770.*
Collins et al., PNAS 1995 vol. 92, pp. 11563-11567.*
Tao et al., Virology 1996, vol. 220, pp. 69-77.*
Matanin et al., "Purification of the major envelop protein GP5 of porcine reproductive and respiratory syndrome virus (PRRSV) from native virions". Journal of Virological Methods, vol. 147, 2008, pp. 127-135.
Pesch et al., "New insights into the genetic diversity of European porcine reproductive and respiratory syndrome virus (PRRSV)". Veterinary Microbiology, vol. 107, 2005, pp. 31-48.
Darwich et al., "Genetic and immunobiological diversities of porcine reproductive and respiratory syndrome genotype I strains". Veterinary Microbiology, vol. 150, 2011, pp. 49-62.
Heath, et al., "The Behaviour of Some Influenza Viruses in Tissue Cultures of Kidney Cells of Various Species". Archiv. f. Virusforschung Bd. VIII, HS, 1958, pp. 577-591.
Hedger et al., "Swine Vesicular Disease Virus". Virus Infections of Porcines, Elsevier Science Publishers, B.V., 1989, pp. 241-250.
Hennen, J., "Statistical methods for longitudinal research on bipolar disorders". Bipolar Disorders, vol. 5, 2003, pp. 156-168.
Hill, Howard, "Overview and History of Mystery Swine". Proceedings of the Mystery Swine Disease Committee Meeting, Denver, CO, Oct. 6, 1990, pp. 29-40.

(Continued)

*Primary Examiner* — Mary E Mosher
*Assistant Examiner* — Myron Hill
(74) *Attorney, Agent, or Firm* — Michael P. Morris; Joyce L. Morrison

(57) ABSTRACT

An infectious clone based on the genome of a wild-type RNA virus is produced by the process of providing a host cell not susceptible to infection by the wild-type RNA virus, providing a recombinant nucleic acid based on the genome of the wild-type RNA virus, transfecting the host cell with the recombinant nucleic acid and selecting for infectious clones. The recombinant nucleic acid comprises at least one full-length DNA copy or in vitro-transcribed RNA copy or a derivative of either. The infectious clones can be used in single or dual purpose vaccines and in viral vector vaccines.

2 Claims, 4 Drawing Sheets

(56) References Cited

U.S. PATENT DOCUMENTS

| | | | |
|---|---|---|---|
| 5,998,601 | A | 12/1999 | Murtaugh et al. |
| 6,001,370 | A | 12/1999 | Burch et al. |
| 6,015,663 | A | 1/2000 | Wesley et al. |
| 6,042,830 | A | 3/2000 | Chladek et al. |
| 6,080,570 | A | 6/2000 | Chladek et al. |
| 6,110,467 | A | 8/2000 | Paul et al. |
| 6,110,468 | A | 8/2000 | Collins et al. |
| 6,197,310 | B1 | 3/2001 | Wensvoort et al. |
| 6,241,990 | B1 | 6/2001 | Collins et al. |
| 6,251,397 | B1 | 6/2001 | Paul et al. |
| 6,251,404 | B1 | 6/2001 | Paul et al. |
| 6,268,199 | B1 | 7/2001 | Meulenberg et al. |
| 6,380,376 | B1 | 4/2002 | Paul et al. |
| 6,391,314 | B1 | 5/2002 | Allan et al. |
| 6,455,245 | B1 | 9/2002 | Wensvoort et al. |
| 6,495,138 | B1 | 12/2002 | van Nieuwstadt et al. |
| 6,498,008 | B2 | 12/2002 | Collins et al. |
| 6,500,662 | B1 | 12/2002 | Calvert et al. |
| 6,592,873 | B1 | 7/2003 | Paul et al. |
| 6,641,819 | B2 | 11/2003 | Mengeling et al. |
| 6,660,513 | B2 | 12/2003 | Mengeling et al. |
| 6,773,908 | B1 | 8/2004 | Paul et al. |
| 6,806,086 | B2 | 10/2004 | Wensvoort et al. |
| 6,841,364 | B2 | 1/2005 | Yuan et al. |
| 6,855,315 | B2 | 2/2005 | Collins et al. |
| 6,982,160 | B2 | 1/2006 | Collins et al. |
| 7,018,638 | B2 | 3/2006 | Chu et al. |
| 7,081,342 | B2 | 7/2006 | Mengeling et al. |
| 7,109,025 | B1 | 9/2006 | Eloit et al. |
| 7,122,347 | B2 | 10/2006 | Verheije et al. |
| 7,132,106 | B2 | 11/2006 | Calvert et al. |
| 7,169,394 | B2 | 1/2007 | Chu et al. |
| 7,211,379 | B2 | 5/2007 | Ellis et a |
| 7,232,680 | B2 | 6/2007 | Calvert et al. |
| 7,264,804 | B2 | 9/2007 | Collins et al. |
| 7,273,617 | B2 | 9/2007 | Yuan et al. |
| 7,312,030 | B2 | 12/2007 | van Rijn et al. |
| 7,335,361 | B2 | 2/2008 | Liao et al. |
| 7,335,473 | B2 | 2/2008 | Wensvoort et al. |
| 7,368,117 | B2 | 5/2008 | Fetzer et al. |
| 7,632,636 | B2 | 12/2009 | Roof et al. |
| 7,722,878 | B2 | 5/2010 | Vaughn et al. |
| 7,897,343 | B2 | 3/2011 | Wensvoort et al. |
| 2002/0012670 | A1 | 1/2002 | Elbers et al. |
| 2002/0098573 | A1 | 7/2002 | Meulenberg et al. |
| 2002/0172690 | A1 | 11/2002 | Calvert et al. |
| 2003/0049274 | A1 | 3/2003 | Meulenberg et al. |
| 2003/0118608 | A1 | 6/2003 | Wensvoort et al. |
| 2003/0157689 | A1 | 8/2003 | Calvert et al. |
| 2003/0219732 | A1 | 11/2003 | van Rijn et al. |
| 2004/0009190 | A1 | 1/2004 | Elbers et al. |
| 2004/0132014 | A1 | 7/2004 | Wensvoort et al. |
| 2004/0197872 | A1 | 10/2004 | Meulenberg et al. |
| 2004/0213805 | A1 | 10/2004 | Verheije |
| 2004/0224327 | A1 | 11/2004 | Meulenberg et al. |
| 2004/0253270 | A1 | 12/2004 | Meng et al. |
| 2006/0063151 | A1 | 3/2006 | Roof et al. |
| 2006/0205033 | A1 | 9/2006 | Meulenberg et al. |
| 2006/0240041 | A1 | 10/2006 | Meulenberg et al. |
| 2006/0286123 | A1 | 12/2006 | Fetzer et al. |
| 2007/0003570 | A1 | 1/2007 | Murtaugh et al. |
| 2007/0042000 | A1 | 2/2007 | Mengeling et al. |
| 2009/0148474 | A1 | 6/2009 | Roof et al. |
| 2010/0003278 | A1 | 1/2010 | Roof et al. |
| 2010/0028860 | A1 | 2/2010 | Roof et al. |
| 2010/0129398 | A1 | 5/2010 | Klinge et al. |
| 2011/0104201 | A1 | 5/2011 | Mengeling et al. |
| 2011/0117129 | A1 | 5/2011 | Roof et al. |
| 2011/0195088 | A1 | 8/2011 | Roof et al. |

FOREIGN PATENT DOCUMENTS

| | | | |
|---|---|---|---|
| EP | 208672 | A1 | 1/1987 |
| EP | 0440219 | A1 | 8/1991 |
| EP | 0529584 | A2 | 3/1993 |
| EP | 587780 | A1 | 3/1994 |
| EP | 0595436 | A2 | 5/1994 |
| EP | 0610250 | A1 | 8/1994 |
| EP | 676467 | A2 | 10/1995 |
| EP | 732340 | A2 | 9/1996 |
| EP | 0835929 | A1 | 4/1998 |
| EP | 0835930 | A1 | 4/1998 |
| EP | 0839912 | A1 | 5/1998 |
| EP | 1018557 | A2 | 7/2000 |
| FR | 2602791 | A1 | 2/1988 |
| GB | 2282811 | A | 4/1995 |
| GB | 2289279 | A | 11/1995 |
| JP | 62/198626 | A | 9/1987 |
| WO | 8803410 | A1 | 5/1988 |
| WO | 8908701 | A1 | 9/1989 |
| WO | 9221375 | A1 | 12/1992 |
| WO | 9303760 | A1 | 3/1993 |
| WO | 9306211 | A1 | 4/1993 |
| WO | 9307898 | A1 | 4/1993 |
| WO | 9314196 | A1 | 7/1993 |
| WO | 9418311 | A1 | 8/1994 |
| WO | 9528227 | A1 | 8/1995 |
| WO | 9531550 | A1 | 11/1995 |
| WO | 9604010 | A1 | 2/1996 |
| WO | 9606619 | A1 | 3/1996 |
| WO | 9636356 | A1 | 11/1996 |
| WO | 9640932 | A1 | 12/1996 |
| WO | 9700696 | A1 | 1/1997 |
| WO | 9731651 | A1 | 1/1997 |
| WO | 9731652 | A1 | 9/1997 |
| WO | 9818933 | A1 | 5/1998 |
| WO | 9835023 | A1 | 8/1998 |
| WO | 9850426 | A1 | 11/1998 |
| WO | 9855625 | A1 | 12/1998 |
| WO | 9855626 | A2 | 12/1998 |
| WO | 0053787 | A1 | 9/2000 |
| WO | 0065032 | A1 | 11/2000 |
| WO | 0159077 | A1 | 8/2001 |
| WO | 0190363 | A1 | 11/2001 |
| WO | 02095040 | A1 | 11/2002 |
| WO | 03062407 | A1 | 7/2003 |
| WO | 2006002193 | A2 | 1/2006 |
| WO | 2006034319 | A2 | 3/2006 |
| WO | 2006074986 | A2 | 7/2006 |
| WO | 2007064742 | A2 | 6/2007 |
| WO | 2008109237 | A2 | 9/2008 |
| WO | 2008121958 | A1 | 10/2008 |
| WO | 2010025109 | A1 | 3/2010 |
| WO | 2011128415 | A1 | 10/2011 |

OTHER PUBLICATIONS

Hirsch et al., "Ultrastructure of Human Leukocytes After Simultaneous Fixation with Glutaraldehyde and Osmium Tetroxide and "Postfixation" in Uranyl Acetate". The Journal of Cell Biology, vol. 38, 1968, pp. 615-627.

Hofmann et al., "Propagation of the virus of porcine epidemic diarrhea in cell culture". Journal of Clinical Microbiology, vol. 26, No. 11, Nov. 1988, pp. 2235-2239.

Hofmann et al., "Quantitation, biological and physicochemical properties of cell culture-adapted porcine epidemic diarrhea coronavirus (PEDV)". Veterinary Microbiology, vol. 20, No. 2, Jun. 1989, pp. 131-142.

Honda et al., "A Serological Comparison of 4 Japanese Isolates of Porcine Enteroviruses with the International Reference Strains". The Japanese Journal of Veterinary Science, vol. 52, No. 1, 1990, pp. 49-54.

Horowitz et al., "Anti-schistosome monoclonal antibodies of different isotypes—correlation with cytotoxicity". The EMBO Journal, Vol. 2, No. 2, 1983, pp. 193-198.

Horsfall et al., "General Principles of Animal Virus Multiplication". Viral and Rickettsial Infections of Man, Fourth Edition, J.B. Lippincott Company, Philadelphia, 1965, pp. 239-241.

Horzinek et al., "Studies on the Substructure of Togaviruses: II. Analysis of Equine Arteritis Rubella, Bovine Viral Diarrhea, and Hog Cholera Viruses". Archiv Für die gesamte Virusforschung, vol. 33, 1971, pp. 306-318.

Hoshino et al., "Isolation and characterization of an equine rotavirus". Journal of Clinical Microbiology, vol. 18, No. 3, Sep. 1983, pp. 585-591.

Hoshino et al., "Serotypic Similarity and Diversity of Rotaviruses of Mammalian and Avian Origin as Studied by Plaque-Reduction Neutralization". The Journal of Infectious Diseases, vol. 149, No. 5, May 1984, pp. 694-702.
Hsue et al., "Characterization of an Essential RNA Secondary Structure in the 3' Untranslated Region of the Murine Coronavirus Genome". Journal of Virology, vol. 74, No. 15, Aug. 2000, pp. 6911-6921.
Huang et al., "Polypyrimidine Tract-Binding Protein Binds to the Complementary Strand of the Mouse Hepatitis Virus 39 Untranslated Region, Thereby Altering RNA Conformation". Journal of Virology, vol. 73, No. 11, Nov. 1999, pp. 9110-9116.
Hurrelbrink et al., "Attenuation of Murray Valley Encephalitis Virus by Site-Directed Mutagenesis of the Hinge and Putative Receptor-Binding Regions of the Envelope Protein". Journal of Virology, vol. 75, No. 16, Aug. 2001, pp. 7692-7702.
Hwang et al., "A 68-Nucleotide Sequence within the 39 Noncoding Region of Simian Hemorrhagic Fever Virus Negative-Strand RNA Binds to Four MA104 Cell Proteins". Journal of Virology, vol. 72, No. 5, May 1998, pp. 4341-4351.
Hyllseth, B., "Structural Proteins of Equine Arteritis Virus". Archiv Für die gesamte Virusforschung, vol. 30, 1973, pp. 177-188.
Iltis et al., "Persistent Varicella-Zoster virus infection in a human rhabdomyosarcoma cell line and recovery of a plaque variant". Infection and Immunity, vol. 37, No. 1, Jul. 1982, pp. 350-358.
Imagawa et al., "Isolation of Foal Rotavirus in MA-104 Cells". Bulleting of Equine Research Institute, vol. 18, 1981, pp. 119-128.
International Preliminary Examination Report for PCT/NL00/00152 mailed May 29, 2001.
International Preliminary Examination Report for PCT/NL02/00314 mailed Aug. 26, 2003.
International Search Report for PCT/NL1997/00593 mailed on Mar. 6, 1998.
International Search Report for PCT/NL2000/00152 mailed on Jul. 6, 2000.
Izeta et al., "Replication and Packaging of Transmissible Gastroenteritis Coronavirus-Derived Synthetic Minigenomes". Journal of Virology, vol. 73, No. 2, Feb. 1999, pp. 1535-1545.
Jackwood et al., "Replication of Infectious Bursal Disease Virus in Continuous Cell Lines". Avian Diseases, vol. 31, No. 2, Apr.-Jun. 1987, pp. 370-375.
Johnson et al., "Feline panleucopaenia virus. IV. Methods for obtaining reproducible in vitro results". Research in Veterinary Science, vol. 8, No. 2, Apr. 1967, pp. 256-264.
Johnson et al., "Pathogenic and humoral immune responses to porcine reproductive and respiratory syndrome virus (PRRSV) are related to viral load in acute infection". Veterinary Immunology and Immunopathology, vol. 102, No. 3, PRRS Immunology and Immunopathology Special Issue, Dec. 2004, pp. 233-247.
Johnston et al., "Genetic to genomic vaccination". Vaccine, vol. 15, No. 8, 1997, pp. 808-809.
Joo et al., "Encephalomyocarditis Virus As a Potential Cause for Mystery Swine Disease", Livestock Conservation Institute, Proceedings of the Mystery Swine Disease Committee Meeting, Denver, CO, Oct. 6, 1990, pp. 62-66.
Jun et al., "Comparison of Dynamics in Viremia Levels in Chickens Inoculated with Marek's Disease Virus Strains of Different Pathotypes". Virologica Sinica, vol. 16, No. 1, Mar. 2001, pp. 59-63.
Jusa et al., "Effect of heparin on infection of cells by porcine reproductive and respiratory syndrome virus". American Journal of Veterinary Research, vol. 58, No. 5, May 1997, pp. 488-491.
Just et al., "A/New Jersey/76 influenza vaccine trial in seronegative schoolchildren: Comparison of a subunit vaccine with a whole-virus vaccine". Medical Microbiology and Immunology, vol. 164, No. 4, 1978, pp. 277-284.
Kang et al., "Primary Isolation and Identification of Avian Rotaviruses from Turkeys Exhibiting Signs of Clinical Enteritis in a Continuous MA-104 Cell Line". Avian Diseases, vol. 30, 1986, pp. 494-499.
Kapur et al., "Genetic variation in porcine reproductive and respiratory syndrome virus isolates in the midwestern United States". Journal of General Virology, vol. 77, 1996, pp. 1271-1276.
Kasza et al., "Establishment, viral susceptibility and biological characteristics of a swine kidney cell line SK-6". Research in Veterinary Science, vol. 13, No. 1, Jan. 1972, pp. 46-51.
Kasza et al., "Isolation and Characterization of a Rotavirus from Pits". Veterinary Record, vol. 87, 1970, pp. 681-686.
Katz et al., "Antigenic differences between European and American isolates of porcine reproductive and respiratory syndrome virus (PRRSV) are encoded by the carboxyterminal portion of viral open reading frame 3". Veterinary Microbiology, vol. 44, No. 1, Apr. 1995, pp. 65-76.
Keffaber, K., "Reproductive Failure of Unknown Etiology"., AASP Newsletter, vol. 1, No. 2, Sep.-Oct. 1989, pp. 1, 4-5, 8-10.
Keffaber, K.K., "Swine Reproductive Failure of Unknown Etiology". The George A. Young Swine Conference & Annual Nebraska SPF Swine Conference, Aug. 13-14, 1990, pp. 55-67.
Key et al., "Genetic variation and phylogenetic analyses of the ORF5 gene of acute porcine reproductive and respiratory syndrome virus isolates". Veterinary Microbiology, vol. 83, 2001, pp. 249-263.
Kim et al., "Analysis of cis-Acting Sequences Essential for Coronavirus Defective Interfering RNA Replication". Virology, vol. 197, No. 1, Nov. 1993, pp. 53-63.
Kim et al., "Different Biological Characteristics of Wild-Type Porcine Reproductive and Respiratory Syndrome Viruses and Vaccine Viruses and Identification of the Corresponding Genetic Determinants". Journal of Clinical Microbiology, vol. 46, No. 5, May 2008, pp. 1758-1768.
Kim et al., "Enhanced replication of porcine reproductive and respiratory syndrome (PRRS) virus in a homogeneous subpopulation of MA-104 cell line". Archives of Virology, vol. 133, 1993, pp. 477-483.
Klein et al., "Deletion of the IgH enhancer does not reduce immunoglobulin heavy chain production of a hybridoma IgD class switch variant". The EMBO Journal, vol. 3, No. 11, Nov. 1984, pp. 2473-2476.
Klinge et al, "Age-dependent resistance to Porcine reproductive and respiratory syndrome virus replication in swine". Virology Journal, vol. 6, No. 177, Oct. 2009.
Klinge et al., "PRRSV replication and subsequent immune responses in swine of various ages". Abstract of Poster No. 56, International Porcine Reproductive and Respiratory Syndrome (PRRS) Symposium, PRRS and PRRSV-Related Diseases: Prevention and Control Strategies, Chicago, IL, Nov. 30-Dec. 1, 2007.
Klovins et al., "A Long-range Pseudoknot in Qb RNA is Essential for Replication". Journal of Molecular Biology, vol. 294, 1999, pp. 875-884.
Klump et al., "Complete Nucleotide Sequence of Infectious Coxsackievirus B3 cDNA: Two Initial 5' Uridine Residues Are Regained during Plus-Strand RNA Synthesis". Journal of Virology, vol. 64, No. 4, Apr. 1990, pp. 1573-1583.
Klupp et al., "Sequence and expression of the glycoprotein gH gene of pseudorabies virus". Virology, vol. 182, No. 2, Jun. 1991, pp. 732-741.
Duan et al., "Identification of a putative Receptor for Porcine Reproductive and Respiratory Syndrome Virus on Porcine Alveolar Macrophages". Journal of Virology, vol. 72, No. 5, May 1998, pp. 4520-4523.
Duran et al. "Recombinant Baculovirus Vaccines Against Porcine Reproductive and Respiratory Syndrome (PRRS)". Abstracts PRRS, Aug. 9th to 10th, 1995, Copenhagen, Denmark, 2 pages.
Dykhuizen et al., "Determining the Economic Impact of the 'New' Pig Disease", Porcine Reproductive and Respiratory Syndrome, a Report on the Seminar Held in Brussels on Nov. 4-5, 1991 and Organized by the European Commission, pp. 53-60.
Easterday, B.C., "Swine Influenza". Diseases of Swine, Sixth Edition, Iowa State University Press, 1986, pp. 244-315. (Part One of Two-pp. 244-285). This NPL is too large for EFS submission. Therefore filing in two parts.
Easterday, B.C., "Swine Influenza". Diseases of Swine, Sixth Edition, Iowa State University Press, 1986, pp. 244-315. (Part Two of Two-pp. 286-315). This NPL is too large for EFS submission. Therefore filing in two parts.
Easterday, et al., "Swine Influenza". In Diseases of Swine (8th Edition), BE Straw, S D'Allaire, WI. Mengeling, DJ Taylor, eds., Ames: Iowa State University Press, 1999, pp. 277-290.

Edwards et al., "Oligodeoxyribonucleotide ligation to single-stranded cDNAs: a new tool for cloning 5' ends of mRNAs and for constructing cDNA libraries by in vitro amplification". Nucleic Acids Research, vol. 19, No. 19, pp. 5227-5232.
Ehresmann et al., "RNA synthesized in calicivirus-infected cells is atypical of picornaviruses". Journal of Virology, vol. 22, No. 2, May 1977, pp. 572-576.
Ellis, R.W., "New Technologies for Making Vaccines". Vaccines, Chapter 29, Plotkin et al Eds., WB Saunders Company, Philadelphia, PA, 1988, pp. 568-575.
Enjuanes et al., "Isolation and Properties of the DNA of African Swine Fever (ASF) Virus". Journal of General Virology, vol. 32, No. 3, Sep. 1976, pp. 479-492.
*Enzo Biochem Inc.*v. *Gen-Probe Incorporated et al.,* No. 01-01230; Decided Jul. 15, 2002.
Estes et al., "Simian rotavirus SA11 replication in cell cultures". Journal of Virology, vol. 31, No. 3, Sep. 1979, pp. 810-815.
Fang et al., "Heterogeneity in nsp2 of European-like porcine reproductive and respiratory syndrome viruses isolated in the United States". Virus Research, vol. 100, 2004, pp. 229-235.
Fenner et al., "Immunization against Viral Diseases", Veterinary Virology, Ch. 14, 1992, pp. 265-271.
Fenner et al., "Viral Genetics and Evolution", Veterinary Virology, Ch. 5, 1992, pp. 89-95.
Ferrari et al., "Isolation of Cytopathic Strains of Rotavirus from Pigs". Microbiologica, vol. 9, No. 3, Jul. 1986, pp. 287-294.
Flint et al., "Virus Cultivation, Detection, and Genetics". Virology, Molecular Biology, Pathogenesis, and Control, Ch. 2, 2000, pp. 40-42.
Foss et al., "Adjuvant Danger Signals Increase the Immune Response to Porcine Reproductive and Respiratory Syndrome Virus". Viral Immunology, vol. 15, No. 4, 2002, pp. 557-566.
Frolov et al., "Alphavirus-based expression vectors: Strategies and applications". Proceedings of the National Academy of Sciences, vol. 93, Oct. 1996, pp. 11371-11377.
Fu et al., "Detection and survival of group a rotavirus in a piggery". Veterinary Record, vol. 125, 1989, pp. 576-578.
Fukuhara et al., "Evidence for endocytosis-independent infection by human rotavirus". Archives of Virology, vol. 97, Nos. 1-2, 1987, pp. 93-99.
Funkhouser et al., "Mutations in the 5'-noncoding, 2C and P3 Regions of the Genome Increase the Efficiency of Hepatitis A Virus Growth in MRC-5 Cells". Vaccines, vol. 94, Cold Springs Harbor Laboratory Press, 1994, pp. 345-349.
Garwes, D.J., "Transmissible gastroenteritis". Veterinary Record, vol. 122, 1988, pp. 462-463.
Geisbert et al., "Use of Immunoelectron Microscopy to Show Ebola Virus During the 1989 United States Epizootic". Journal of Clinical Pathology, vol. 43, No. 10, Oct. 1990, pp. 813-816.
Girard et al., "Experimentally induced porcine proliferative and necrotising pneumonia with an influenza A virus". The Veterinary Record, vol. 130, Mar. 1992, pp. 206-207.
Godeny et al., "Map location of lactate dehydrogenase-elevating virus (LDV) capsid protein (VPL) gene", Virology, vol. 177, No. 2, Aug. 1990, pp. 768-771.
Godeny et al., "The 3' Terminus of Lactate Dehydrogenase-Elevating Virus Genome RNA Does Not Contain Togavirus or Flavivirus Conserved Sequences", Virology, vol. 72, 1989, pp. 647-650.
Goldfield et al., "Influenza in New Jersey in 1976: Isolations of Influenza A/New Jersey/76 Virus at Fort Dix"The Journal of Infectious Diseases, vol. 136, Supp. 3, 1977, pp. S347-S355.
Goldstein, et al., "Evaluation of Three Cell Culture Systems as Substrates for Influenza Virus Assay". Applied Microbiology, vol. 19, No. 4, Apr. 1970, pp. 580-582.
Gong et al., "Characterization of RNA synthesis during a one-step growth curve and of the replication mechanism of bovine viral diarrhoea virus". Journal of General Virology, vol. 77, 1996, pp. 2729-2736.
Gorcyca et al., RespPRRS: A new tool for the prevention and control of PRRS in pigs. Proceedings of the American Association of Swine Practitioners, Omaha, Nebraska, Mar. 1995, pp. 1-22.
Gourreau et al., "Diffusion du virus de la grippe du porc (H1N1=Hsw1N1) en France". Annales de l'Institut Pasteur/Virologie, vol. 132, No. 2, Apr.-Jun. 1981, pp. 287-294.
Goyal, S., "Porcine Reproductive and Respiratory Syndrome", Journal of Veterinary Diagnostic Investigation, vol. 5, No. 4, 1993, pp. 656-664.
Gravell et al., "Differences among isolates of simian hemorrhagic fever (SHF) virus". Proceedings of the Society for Experimental Biology and Medicine, vol. 181, No. 1, 1986, pp. 112-119.
Graves, J.H., "Swine Vesicular Disease". Diseases of Swine, Fifth Edition, Chapter 23, The Iowa State University Press, Ames, Iowa, 1958, pp. 288-293.
Grebennikova et al., "Genomic characterization of virulent, attenuated, and revertant passages of a North American porcine reproductive and respiratory syndrome virus strain". Virology, vol. 321, 2004, pp. 383-390.
Greiner et al., "Quantitative relationship of systemic virus concentration on growth and immune response in pigs". Journal of Animal Science, vol. 78, 2000, pp. 2690-2695.
Grizzard et al., "Experimental production of respiratory tract disease in cebus monkeys after intratracheal or intranasal infection with influenza A/Victoria/3/75 or influenza a/New Jersey/76 virus". Infection and Immunity, vol. 21, No. 1, Jul. 1978, pp. 201-205.
Grouse, L.D., "Swine Flue Sequelae"., Journal of the American Medical Association, vol. 243, No. 24, 1980, p. 2489.
Grunert et al., "Sensitivity of Influenza A/New Jersey/8/76 (HswlNl) Virus to Amantadine-HCI". Journal of Infectious Diseases, vol. 136, No. 2, 1977, pp. 297-300.
Guan et al., "Requirement of a 5?-Proximal Linear Sequence on Minus Strands for Plus-Strand Synthesis of a Satellite RNA Associated with Turnip Crinkle Virus". Virology, vol. 268, No. 2, Mar. 2000, pp. 355-363.
Gubler et al., "A simple and very efficient method for generating cDNA libraries". Gene, vol. 25, 1983, pp. 263-269.
Gustafson, D.P., "Pseudorabies". Diseases of Swine, Fifth Edition, Ch. 14, The Iowa State University Press, Ames, Iowa, 1981, pp. 209-223.
Halbur et al., "Comparative pathogenicity of nine US porcine reproductive and respiratory syndrome virus (PRRSV) isolates in a five-week-old cesarean-derived, colostrum-deprived pig model". Journal of Veterinary Diagnostic Investigation, vol. 8, 1996, pp. 11-20.
Halbur et al., "Effects of different US isolates of porcine reproductive and respiratory syndrome virus (PRRSV) on blood and bone marrow parameters of experimentally infected pigs". Veterinary Record, vol. 151, 2002, pp. 344-348.
Halbur et al., "Variable Pathogenicity of Nine Porcine Reproductive and Respiratory Syndrome Virus (PRRSV) Isolates". Conference of Research Workers in Animal Diseases, Abstracts of Papers, Chicago, Illinois, paper #222, Nov. 1993.
Halbur et al., "Viral Pneumonia in Neonatal and Nursery pigs. Experimental Work with SIRS Agent and Evidence of Another New Viral Agent". Agri-Practice, vol. 12, No. 1, Jan.-Feb. 1991, pp. 23-34.
Hao et al., "Polymorphic genetic characterization of the ORF7 gene of porcine reproductive and respiratory syndrome virus (PRRSV) in China". Virology Journal, vol. 8:73, pp. 1-9.
Harlow & Lane, Editors, "Antibodies, A Laboratory Manual". Cold Spring Harbor: Cold Spring Harbor Laboratory, New York, 1988, pp. 423, 464-468.
Haynes et al., "Temporal and Morphologic Characterization of the Distribution of Porcine Reproductive and Respiratory Syndrome Virus (PRRSV) by In Situ Hybridization in Pigs Infected with Isolates of PRRSV that Differ in Virulence". Veterinary Pathology, vol. 34, 1997, pp. 39-43.
Carvajal et al., "Evaluation of a Blocking ELISA Using Monoclonal Antibodies for the Detection of Porcine Epidemic Diarrhea Virus and Its Antibodies". Journal of Veterinary Diagnostic Investigation, vol. 7, No. 1, Jan. 1995, pp. 60-64.
Cavanagh, D., "Nidovirales: A new order comprising Coronaviridae and Arteriviridae". Archives of Virology, vol. 142, No. 3, 1997, pp. 629-633.
Chang et al., "A cis-Acting Function for the Coronavirus Leader in Defective Interfering RNA Replication". Journal of Virology, vol. 68, No. 12, Dec. 1994, pp. 8223-8231.

Chang et al., "Evolution of Porcine Reproductive and Respiratory Syndrome Virus during Sequential Passages in Pigs". Journal of Virology, vol. 76, No. 10, May 2002, pp. 4750-4763.
Chao et al., "Monoclonal Antibodies to Metacyclic Stage Antigens of Trypanosoma Cruzi" The American Journal of Tropical Medicine and Hygiene, vol. 34, No. 4, Jul. 1985, pp. 694-701.
Charley, B., "Interaction of influenza virus with swine alveolar macrophages: Influence of anti-virus antibodies and cytochalasin B". Annales de l'Instiut Pasteur. Virologie, vol. 134, No. 1, Jan. 1983, pp. 51-59.
Chasey et al., "Replication of Atypical Ovine Rotavirus in Small Intestine and Cell Culture". Journal of General Virology, vol. 67, No. 3, Mar. 1986, pp. 567-576.
Chen et al., "Determination of the 5' end of the lactate dehydrogenase-elevating virus genome by two independent approaches". Journal of General Virology, vol. 75, 1994, pp. 925-930.
Christianson et al., "Experimental Reproduction of a Newly Described Viral Disease, Swine Infertility and Respiratory Syndrome (SIRS), in Pregnant Sows". 72nd Annual Meeting of the Conference of Research Workers in Animal Disease, Chicago, IL, Nov. 11 & 12, 1991, p. 48, Abstract No. 269.
Christianson et al., "Experimental reproduction of swine infertility and respiratory syndrome in pregnant sows". American Journal of Veterinary Research, vol. 53, No. 4, Apr. 1992, pp. 485-488.
Christianson et al., "Porcine reproductive and respiratory syndrome: A review"., Journal of Swine Health and Production, vol. 2, No. 2, Mar. and Apr. 1994, pp. 10-28.
Christianson et al., "Swine Infertility and Respiratory Syndrome". Pig Veterinary Journal, vol. 27, No. 9, Apr. 1991, pp. 9-12.
Chutivongse et al., "One-year study of the 2-1-1 intramuscular postexposure rabies vaccine regimen in 100 severely exposed Thai patients using rabies immune globulin and Vero cell rabies vaccine". Vaccine, vol. 9, No. 8, Aug. 1991, pp. 573-576.
Clark et al., "Trypsin enhancement of rotavirus infectivity: mechanism of enhancement". Journal of Virology, vol. 39, No. 3, Sep. 1981, pp. 816-822.
Collins et al., "Experimental Transmission of Swine Reproductive Failure Syndrome (Mystery Swine Disease) in Gnotobiotic Piglets". 71st Annual Meeting of the Conference of Research Workers in Animal Disease, Chicago, IL, Nov. 5-6, 1990, Abstract No. 2.
Collins et al., "Isolation of swine infertility and respiratory syndrome virus (isolate ATCC VR-2332) in North America and experimental reproduction of the disease in gnotobiotic pigs". Journal of Veterinary Diagnostic Investigation, vol. 4, 1992, pp. 117-126.
Collins et al., "Respiratory Disease in a Swine Herd Experiencing a Reproductive Failure Syndrome". Minnesota Swine Conference for Veterinarians, Sep. 16-18, 1990, pp. 206-207.
Collins et al., "Swine Diagnostic Pathology". Allen D. Leman Swine Conference, College of Veterinary Medicine, University of Minnesota, Sep. 18-22, 1998, pp. 1-4.
Collins et al., "Swine Infertility and Respiratory Syndrome (Mystery Swine Disease)". Minnesota Swine Conference for Veterinarians, St. Paul, MN, Sep. 15-17, 1991, pp. 200-205.
Collins, J.E., "Newly Recognized Respiratory Syndromes in North American Swine Herds". American Association of Swine Practitioners Newsletter, vol. 3, No. 7, Sep.-Oct. 1991, pp. 7, 10-11.
Conner et al., "Isolation and characteristics of an equine reovirus type 3 and an antibody prevalence survey to reoviruses in horses located in New York State". Veterinary Microbiology, vol. 9, No. 1, Feb. 1984, pp. 15-25.
Conzelmann et al., "Molecular Characterization of Porcine Reproductive and Respiratory Syndrome Virus, a Member of the Arterivirus Group". Virology, vol. 193, 1993, pp. 329-339.
Cooper et al., "Porcine Reproductive and Respiratory Syndrome: NEB-1 PRRSV Infection did not Potentiate Bacterial Pathogens". Journal of Veterinary Diagnostic Investigation, vol. 7, No. 3, Jul. 1995, pp. 313-320.
Corn et al., "Isolation of Vesicular Stomatitis Virus New Jersey Serotype from Phlebotomine Sand Files in Georgia". The American Journal of Tropical Medicine and Hygiene, vol. 42, No. 5, May 1990, pp. 476-482.
Dacso, et al., "Sporadic occurrence of zoonotic swine influenza virus infections". Journal of Clinical Microbiology, vol. 20, No. 4, Oct. 1984, pp. 833-835.
Database WPIL Week 8702, Derwent Publications Ltd., London, GB; AN 87-009295 [2] & EP, A,208672 (Regional Wallone-Chiron Corp, Wallone Regional) Jan. 14, 1987.
Database WPIL Week 8741, Derwent Publications Ltd., London, GB; AN 87-286929 [41] & EP, A,62, 198626 (Za Bieseibutsu Kagaku Ken) Sep. 2, 1987.
Database WPIL Week 8821, Derwent Publications Ltd., London, GB; AN 88-147502 [21] & WO,A,8 803 410 (Inst Pasteur) May 19, 1988.
De Mazancourt et al., "Antibody response to the rubella virus structural proteins in infants with the congenital rubella syndrome". Journal of Medical Virology, vol. 19, No. 2, Jun. 1986, pp. 111-122.
De Vries et al., "Genetic Manipulation of Equine Arteritis Virus Using Full-Length cDNA Clones: Separation of Overlapping Genes and Expression of a Foreign Epitope". Virology, vol. 270, No. 1, 2000, pp. 84-97.
De Vries et al., "The Genome Organization of the Nidovirales: Similarities and Differences between Arteri-, Toro-, and Coronaviruses". Seminars in Virology, vol. 8, 1997, pp. 33-47.
De Vries, et al., "All subgenomic mRNAs of equine arteritis virus contain a common leader sequence". Nucleic Acids Research, vol. 18, No. 11, 1990, pp. 3241-3247.
Dea et al., "Antigenic Variability among North American and European Strains of Porcine Reproductive and Respiratory Syndrome Virus as Defined by Monoclonal Antibodies to the Matrix Protein". Journal of Clinical Microbiology, vol. 34, No. 5, Jun. 1996, pp. 1488-1493.
Dea et al., "Antigenic variant of swine influenza virus causing proliferative and necrotizing pneumonia in pigs". Journal of Veterinary Diagnostic Investigation, vol. 4, No. 4, 1992, pp. 380-392.
Dea et al., "Caracteristiques d'Isolats des virus influenza et de l'encephalomyocardite associes au Syndrome Reproducteur et Respiratoire Porcine (S.R.R.P.) au Quebec.sup.a," Le Medecin Veterinaire Du Quebec, vol. 21, No. 4, Nov. 1991, pp. 170-175.
Dea et al., "Current knowledge on the structural proteins of porcine reproductive and respiratory syndrome (PRRS) virus: comparison of the North American and European isolate". Archives of Virology, vol. 145, No. 4, Apr. 2000, pp. 659-688.
Dea et al., "Isolation of encephalomyocarditis virus among stillborn and post-weaning pigs in Quebec". Archives of Virology, vol. 117, Nos. 1-2, 1991, pp. 121-128.
Dea et al., "Swine reproductive and respiratory syndrome in Quebec: Isolation of an enveloped virus serologically-related to Lelystad virus". Canadian Veterinary Journal, vol. 33, No. 12, Dec. 1992, pp. 801-808.
Dea et al., "Virus Isolations from Farms in Quebec Experiencing Severe Outbreaks of Respiratory and Reproductive Problems". Proceedings of the Mystery Swine Disease Committee Meeting, Denver, CO, Oct. 6, 1990, pp. 67-72.
Del Val et al., "Glycosylated components of African swine fever virus particles". Virology, vol. 152, No. 1, Jul. 1986, pp. 39-49.
Den Boon et al., "Equine Arteritis Virus Is Not a Togavirus but Belongs to the Coronaviruslike Superfamily". Journal of Virology, vol. 65, No. 6, 1991, pp. 2910-2920.
Den Boon et al., "Processing and Evolution of the N-Terminal Region of the Arterivirus Replicase ORF1a Protein: Identification of Two Papainlike Cysteine Proteases". Journal of Virology, vol. 69, No. 7, Jul. 1995, pp. 4500-4505.
Deng et al., "An improved procedure for utilizing terminal transferase to add homopolymers to the 38 termini of DNA". Nucleic Acids Research, vol. 9, No. 16, 1981, pp. 4173-4188.
Derbyshire, J.B. "Porcine Enterovirus Infections". Diseases of Swine, Fifth Edition, Chapter 20, 1981, pp. 265-270.
Devereux et al., "A Comprehensive Set of Sequence Analysis Programs for VAX". Nucleic Acids Research, vol. 12, No. 1, 1984, pp. 387-395.
Dianzani et al., "Is Human Immunodeficiency Virus RNA Load Composed of Neutralized Immune Complexes". The Journal of Infectious Diseases, vol. 185, 2002, pp. 1051-1054.

Dildrop et al., "Immunoglobulin V region variants in hybridoma cells. II. Recombination between V genes". The EMBO Journal, vol. 1, No. 5, 1982, pp. 635-640.
Dreher, T.W., "Functions of the 3'-Untranslated Regions of Positive Strand RNA Viral Genomes". Annual Review of Phytopathology, vol. 37, 1999, pp. 151-174.
Drew et al., "Production, characterization and reactivity of monoclonal antibodies to porcine reproductive and respiratory syndrome virus". Journal of General Virology, vol. 76, 1995, pp. 1361-1369.
Drew, T., "Porcine Reproductive and Respiratory Syndrome Virus: A Review". Apr. 1996, 3 pages.
Rice et al., "Production of Infectious RNA Transcripts from Sindbis Virus cDNA Clones: Mapping of Lethal Mutations, Rescue of a Temperature-Sensitive Marker, and in Vitro Mutagenesis to Generate Defined Mutants". Journal of Virology, vol. 61, No. 12, Dec. 1987, pp. 3809-3819.
Roberts et al., "Abortion in Swine". Veterinary Ostetrics and Genital Diseases, Edwards Brothers, Inc., Ann Arbor, 1986, pp. 180-192.
Roof et al., "Efficacy of Modified Live Virus Porcine Reproductive and Respiratory Virus Vaccines Against Heterologous Respiratory Challenge". 4th International Symposium on Emerging and Re-emerging Pig Diseases, Rome, Jun. 28-Jul. 2, 2003, pp. 117-118.
Ropp et al., "Characterization of Emerging European-Like Porcine Reproductive and Respiratory Syndrome Virus Isolates in the United States"., Journal of Virology, vol. 78, No. 7, Apr. 2004, pp. 3684-3703.
Rossow et al., "Experimental porcine reproductive and respiratory syndrome virus infection in one-, four-, and 10-week-old pigs". Journal of Veterinary Diagnostic Investigation, vol. 6, 1993, pp. 3-12.
Rossow, K.D., "Porcine Reproductive and Respiratory Syndrome". Veterinary Pathology, vol. 35, 1998, pp. 1-20.
Roth et al., "Influenza virus hemagglutinin expression is polarized in cells infected with recombinant SV40 viruses carrying cloned hemagglutinin DNA". Cell, vol. 33, No. 2, Jun. 1983, pp. 435-443.
Roth et al., "The large external domain is sufficient for the correct sorting of secreted or chimeric influenza virus hemagglutinins in polarized monkey kidney cells". The Journal of Cell Biology, vol. 104, Mar. 1987, pp. 769-782.
Rottier et al., "Predicted Membrane Topology of the Coronavirus Protein E1". Biochemistry, vol. 25, 1986, pp. 1335-1339.
Rovira et al., "Experimental Inoculation of Conventional Pigs with Porcine Reproductive and Respiratory Syndrome virus and Porcine Circovirus 2", J. Virol, jApr. 2002, vol. 76, No. 7, pp. 3232-3239.
Sagripanti et al., "The Cap Structure of Simian Hemorrhagic Fever Virion RNA". Virology, vol. 151, 1986, pp. 143-150.
Saif et al., "Serial propagation of porcine group C rotavirus (pararotavirus) in a continuous cell line and characterization of the passaged virus". Journal of Clinical Microbiology, vol. 26, No. 7, Jul. 1988, pp. 1277-1282.
Saif, L.J., "Coronavirus Immunogens". Veterinary Microbiology, vol. 37, No. 3-4, Nov. 1993, pp. 285-297.
Sarnow, P. "Role of 3'-End Sequences in Infectivity of Poliovirus Transcripts Made in Vitro". Journal of Virology, vol. 63, No. 1, Jan. 1989, pp. 467-470.
Sawicki et al., "Coronavirus Transcription: Subgenomic Mouse Hepatitis Virus Replicative Intermediates Function in RNA Synthesis". Journal of Virology, vol. 64, No. 3, Mar. 1990, pp. 1050-1056.
Schmidt et al., "Infection of Influenza A Viruses of Tracheal Organ Cultures Derived from Homologous and Heterologous Hosts". The Journal of Infectious Diseases, vol. 129, No. 1, 1974, pp. 28-36.
Scott, F.W., "Immunization against feline coronaviruses". Advances in Experimental Medicine and Biology, vol. 218, 1987, pp. 569-576.
Seal et al., "Analysis of the Serologic Relationship among San Miguel Sea Lion Virus and Vesicular Exanthema of Swine Virus Isolates. Application of the Western Blot Assay for Detection of Antibodies in Swine Sera to these Virus Types". Journal of Veterinary Diagnostic Investigation, vol. 7, No. 2, Apr. 1995, pp. 190-195.
Seal et al., "Isolation of caliciviruses from skunks that are antigenically and genotypically related to San Miguel sea lion virus Original Research". Virus Research, vol. 37, No. 1, Jun. 1995, pp. 1-12.
Seneca, H., "Influenza: epidemiology, etiology, immunization and management". Journal of American Geriatrics Society, vol. 28, No. 6, Jun. 1980, pp. 241-250.
Sethna et al., "Coronavirus subgenomic minus-strand RNAs and the potential for mRNA replicons". Proceedings of the National Academy of Sciences, vol. 86, Jul. 1989, pp. 5626-5630.
Setzer et al., "Size Heterogeneity in the 3' End of Dihydrofolate Reductase Messenger RNAs in Mouse Cells". Cell, vol. 22, Nov. 1980, pp. 361-370.
Shaw et al., "Experimental rotavirus infection in three-week-old pigs". American Journal of Veterinary Research, vol. 50, No. 11, Nov. 1989, pp. 1961-1965.
Shen et al., "Determination of the complete nucleotide sequence of a vaccine strain of porcine reproductive and respiratory syndrome virus and identification of the Nsp2 gene with a unique insertion". Archives of Virology, vol. 145, No. 5, May 2000, pp. 871-883.
Shibata et al., "Detection of Human Papilloma Virus in Paraffin-Embedded Tissue Using the Polymerase Chain Reaction". The Journal of Experimental Medicine, vol. 167, No. 1, Jan. 1988, pp. 225-230.
Shieh et al., "The 5'-End Sequence of the Murine Coronavirus Genome: Implications of Multiple Fusion Sites in Leader-Primed Transcription". Virology, vol. 156, 1987, pp. 321-330.
Shin et al., "Assessment of Porcine Reproductive and Respiratory Syndrome Virus RNA Load in Sera and Tissues during Acute Infection". Journal of Veterinary Science, vol. 3, No. 2, 2002, pp. 75-85.
Shope et al., "The Susceptibility of Swine to the Virus of Human Influenza". Annual Meeting of the Society of American Bacteriologists in New York, 1936, pp. 791-801.
Shortridge et al., "Geographical Distribution of Swine (HSw1N1) and Hong Kong (H3N2) Influenza Virus Variants in Pigs in Southeast Asia". Intervirology, vol. 11, No. 1, 1979, pp. 9-15.
Skiadopoulos et al., "Identification of Mutations Contributing to the Temperature-Sensitive, Cold-Adapted, and Attenuation Phenotypes of the Live-Attenuated Cold-Passage 45 (cp45) Human Parainfluenza Virus 3 Candidate Vaccine". Journal of Virology, vol. 73, No. 2, Feb. 1999, pp. 1374-1381.
Smith et al., "Isolation of Swine Influenza Virus from Autopsy Lung Tissue of Man". New England Journal of Medicine, vol. 294, Mar. 1976, pp. 708-710.
Smith et al., "San Miguel Sea Lion Virus Isolation, Preliminary Characterization and Relationship to Vesicular Exanthema of Swine Virus". Nature, vol. 244, Jul. 1973, pp. 108-110.
Snijder et al., "A 3'-Coterminal Nested Set of Independently Transcribed mRNAs Is Generated during Berne Virus Replication". Journal of Virology, vol. 64, No. 1, Jan. 1990, pp. 331-338.
Snijder et al., "Identification of a Novel Structural Protein of Arteriviruses". Journal of Virology, vol. 73, No. 8, Aug. 1999, pp. 6335-6345.
Snijder et al., "Non-structural proteins 2 and 3 interact to modify host cell membranes during the formation of the arterivirus replication complex". Journal of General Virology, vol. 83, 2001, pp. 985-994.
Snijder et al., "Proteolytic Processing of the Replicase ORF1a Protein of Equine Arteritis Virus". Journal of Virology, vol. 68, No. 9, Sep. 1994, pp. 5755-5764.
Snijder et al., "The carboxyl-terminal part of the putative Berne virus polymerase is expressed by ribosomal frameshifting and contains sequence motifs which indicate that toro- and coronaviruses are evolutionarily related". Nucleic Acids Research, vol. 18, No. 15, Aug. 1990, pp. 4535-4542.
Snijder et al., "The molecular biology of arteriviruses". Journal of General Virology, vol. 79, 1998, pp. 961-979.
Snijder et al., "Toroviruses: replication, evolution and comparison with other members of the coronavirus-like superfamily". Journal of General Virology, vol. 74, 1993, pp. 2305-2316.
Spaan et al., "Coronaviruses: Structure and Genome Expression". Journal of General Virology, vol. 69, 1988, pp. 2939-2952.
Stephen et al., "Swine Influenza Virus Vaccine: Potentiation in Rhesus Monkeys in Antibody Responses by a Nuclease Resistant Derivative of Ply I-Poly C". U.S. Army Medical Research Institute of Infectious Diseases, Fort Detrick, Frederick, MD 21701, 1976, 10 pages.

Stephen et al., "Swine influenza virus vaccine: potentiation of antibody responses in rhesus monkeys". Science, vol. 197, No. 4310, 1977, pp. 1289-1290.
Stevenson et al., "Endemic Porcine Reproductive and Respiratory Syndrome Virus Infection of Nursery Pigs in Two Swine Herds without Current Reproductive Failure". Journal of Veterinary Diagnostic Investigation, vol. 5, 1993, pp. 432-434.
Stim, T.B., "Arbovirus Plaquing in Two Simian Kidney Cell Lines". Journal of General Virology, vol. 5, No. 3, Oct. 1969, pp. 329-338.
Suarez et al., "Direct detection of the porcine reproductive and respiratory syndrome (PRRS) virus by reverse polymerase chain reaction (RT-PCR)". Archives of Virology, vol. 135, No. 1-2, 1994, pp. 89-99.
Suarez et al., "Phylogenetic relationships of European strains of porcine reproductive and respiratory syndrome virus (PRRSV) inferred from DNA sequences of putative ORF-5 and ORF-7 genes". Virus Research, vol. 42, Nos. 1-2, Jun. 1996, pp. 159-165.
Sumiyoshi et al., "Infectious Japanese Encephalitis Virus RNA Can Be Synthesized from in Vitro-Ligated cDNA Templates". Journal of Virology, vol. 66, No. 9, Sep. 1992, pp. 5425-5431.
Tahara et al., "Coronavirus Translational Regulation: Leader Affects mRNA Efficiency". Virology, vol. 202, No. 1, Aug. 1994, pp. 621-630.
Tauraso et al., "Simian Hemorrhagic Fever: III. Characterization of a Viral Agent". The American Journal of Tropical Medicine and Hygiene, vol. 17, No. 3, May 1968, pp. 422-431.
Terpstra et al., "Experimental reproduction of porcine epidemic abortion and respiratory syndrome (mystery swine disease) by infection with Lelystad virus: Koch's postulates fulfilled". The Veterinary Quarterly, vol. 13, No. 3, Jul. 1991, pp. 131-136.
Wensvoort et al., "Antigenic Comparison of Lelystad Virus and Swine Infertility and Respiratory Syndrome (SIRS) Virus". Journal of Veterinary Diagnostic Investigation, vol. 4, 1992, pp. 134-138.
Wensvoort et al., "Bovine viral diarrhoea virus infections in piglets born to sows vaccinated against swine fever with contaminated vaccine". Research in Veterinary Science, vol. 45, 1988, pp. 143-148.
Wensvoort et al., "Characterization of Porcine and Some Ruminant Pestiviruses by Cross-neutralization" vol. 20, 1989, pp. 291-306.
Wensvoort et al., "Lelystad virus, the cause of porcine epidemic abortion and respiratory syndrome: a review of mystery swine disease research in Lelystad". Veterinary Microbiology, vol. 33, Nos. 1-4, Nov. 1992, pp. 185-193.
Wensvoort et al., "Mystery Swine Disease in the Netherlands the Isolation of Lelystad Virus". The Veterinary Quarterly, vol. 13, No. 3, 1991, pp. 121-130.
Wensvoort et al., "Production of Monoclonal Antibodies Against Swine Fever Virus and Their Use in Laboratory Diagnosis". Veterinary Microbiology, vol. 12, 1986, pp. 101-108.
Wensvoort et al.,"The Porcine Reproductive and Respiratory Syndrome; Characteristics and diagnosis of the causative virus". Veterinary Biotechnology Newsletter, vol. 3, 1993, pp. 113-120.
Wesley et al., "Differentiation of vaccine (strain RespPRRS) and field strains of porcine reproductive and respiratory syndrome virus by restriction enzyme analysis". Proceedings of the American Association on Swine Practitioners, Nashville, TN, USA, 1996, pp. 141-143.
Westenbrink et al., "An enzyme-linked immunosorbent assay for detection of antibodies to porcine parvovirus". Journal of Virological Methods, vol. 23, 1989, pp. 169-178.
Wieczorek-Krohmer et al., "Porcine reproductive and respiratory syndrome virus (PRRSV): Monoclonal antibodies detect common epitopes on two viral proteins of European and U.S. isolates". Veterinary Microbiology, vol. 51, Nos. 3-4, Aug. 1996, pp. 257-266.
Witte, K.H. "The Situation of 'Epidemic Late Abortion of Swine' in the State of Northrhine-Westphalia". Workshop Seminar, Apr. 1991.
Woode, et al., "Porcine Rotavirus Infection". Diseases of Swine, Fifth Edition, Chapter 26, The Iowa State University Press, Ames, Iowa, 1981, pp. 310-322.
Woods et al., "Antigenicity of Inactivated Swine Influenza Virus Concentrated by Centrifugation". Research Communications in Chemical Pathology and Pharmacology, vol. 13, No. 1, 1976, pp. 129-132.
Woods et al., "Experimental challenge of pregnant gilts with swine influenza virus after vaccination". Research Communications in Chemical Pathology and Pharmacology, vol. 15, No. 4, Dec. 1976, pp. 787-95.
Woods et al., "Investigation of Four Outbreaks of Acute Respiratory Disease in Swine and Isolation of Swine Influenza Virus". Health Laboratory Science, vol. 5, No. 4, Oct. 1968, pp. 218-224.
Wootton et al., "Structure-function of the ORF7 protein of porcine reproductive and respiratory syndrome virus in the viral capsid assembly". Proceedings of the International Symposium on PRRS and Aujeszky's Disease, Ploufragan, France, pp. 37-38.
Yamane et al., "Annual Examination of Influenza Virus Infection Among Pigs in Miyagi Prefecture, Japan: The Appearance of Hsw1N1 Virus". Acta Virologica, vol. 23, 1979, pp. 240-248.
Yang et al., "Comparative sequence analysis of open reading frames 2 to 7 of the modified live vaccine virus and other North American isolates of the porcine reproductive and respiratory syndrome virus". Archives of Virology, vol. 143, 1998, pp. 601-612.
Yoon et al., "A modified serum neutralization test for the detection of antibody to porcine reproductive and respiratory syndrome virus in swine sera". Journal of Veterinary Diagnostic Investigation, vol. 6, No. 3, Jul. 1994, pp. 289-292.
Yoon et al., "Failure to Consider the Antigenic Diversity of Porcine Reproductive and Respiratory Syndrome (PRRS) Virus Isolates May Lead to Misdiagnosis". Journal of Veterinary Diagnostic Investigation, vol. 7, Jul. 1995, pp. 386-387.
Yoon et al., "Isolation of a Cytopathic Virus from Weak Pigs on Farms with a History of Swine Infertility and Respiratory Syndrome". Journal of Veterinary Diagnostic Investigation, vol. 4, Apr. 1992, pp. 139-143.
Yu et al., "Specific Binding of Host Cellular Proteins to Multiple Sites within the 39 End of Mouse Hepatitis Virus Genomic RNA". Journal of Virology, vol. 69, No. 4, Apr. 1995, pp. 2016-2023.
Yuan et al., "Complete genome comparison of porcine reproductive and respiratory syndrome virus parental and attenuated strains". Virus Research, vol. 74, 2001, pp. 99-110.
Yuan et al., "Erratum to 'Complete genome comparison of porcine reproductive and respiratory syndrome virus parental and attenuated strains '[Virus Research 74 (2001) 99-110]". Virus Research, vol. 79, 2001, p.187.
Yuan et al., "Molecular characterization of a highly pathogenic strain of PRRSV associated with porcine High Fever syndrome in China". 2007 International Porcine Reproductive and Respiratory Syndrome (PRRS) Symposium, Chicago, Illinois, Nov.-Dec. 2007, Poster 70.
Yuan et al., American Society for Virology, 16th Annual Meeting, Bozeman, Montana, Jul. 19-23, 1997, Abstract P29-5, p. 229.
Zeijst, et al., "The Genome of Equine Arteritis Virus". Virology, vol. 68, 1975, pp. 418-425.
Zhou et al., "Generation of cytotoxic and humoral immune responses by nonreplicative recombinant Semliki Forest virus". Proceedings of the National Academy of Sciences, vol. 92, Mar. 1995, pp. 3009-3013.
Zimmerman et al., "General overview of PRRSV: A perspective from the United States". Veterinary Microbiology, vol. 55, Nos. 1-4, Apr. 1997, pp. 187-196.
Thacker, B., "Clinical Manifestations of PRRS Virus". 2003 PRRS Compendium: Second Edition, National Pork Board, Des Moines, IA, 2003, pp. 7-15.
Thanawongnuwech et al., "Effects of Low (Modified-live Virus Vaccine) and High (VR-2385)-Virulence Strains of Porcine Reproductive and Respiratory Syndrome Virus on Pulmonary Clearance of Copper Particles in Pigs". Veterinary Pathology, vol. 35, 1998, pp. 398-406.
Theil et al., "Isolation and Serial Propagation of Turkey Rotaviruses in a Fetal Rhesus Monkey Kidney (MA104) Cell Line". Avian Diseases, vol. 30, No. 1, 1985, pp. 93-104.
Theil et al., "Partial characterization of a bovine group A rotavirus with a short genome electropherotype". Journal of Clinical Microbiology, vol. 26, No. 6, Jun. 1988, p. 1094-1099.
Thomson et al., "Ontario. Proliferative and necrotizing pneumonia (PNP) of swine: the Ontario situation". Canadian Veterinary Journal, vol. 32, May 1991, p. 313.

Thouless et al., "Isolation of two lapine rotaviruses: Characterization of their subgroup, serotype and RNA electropherotypes". Archives of Virology, vol. 89, Nos. 1-4, 1986, pp. 161-170.
Tian et al., "Emergence of Fatal PRRSV Variants: Unparalleled Outbreaks of Atypical PRRS in China and Molecular Dissection of the Unique Hallmark". PLoS One, vol. 2, No. 6, e526, 2007, pp. 1-10.
Timony, P.J. "Equine Viral Arteritis", Manual of Standards for Diagnostic Tests and Vaccines, 1992, pp. 493-500.
Tobita et al., "Plaque Assay and Primary Isolation of influenza A Viruses in an Established Line of Canine Kidney Cells (MDCK) in the Presence of Trypsin". Medical Microbiology and Immunology, vol. 162, No. 1, Dec. 1975, pp. 9-14.
Todd et al., "Development of an adjuvant-active nonionic block copolymer for use in oil-free subunit vaccines formulations". Vaccine, vol. 15, No. 5, 1997, pp. 564-570.
Travassos et al., "Carajas and Maraba Viruses, Two New Vesiculoviruses Isolated from Phlebotomine Sand Flies in Brazil". American Journal of Tropical Medicine and Hygiene, vol. 33, No. 5, Sep. 1984, pp. 999-1006.
Tsunemitsu et al., "Isolation, characterization, and serial propagation of a bovine group C rotavirus in a monkey kidney cell line (MA104)". Journal of Clinical Microbiology, vol. 29, No. 11, Nov. 1991, pp. 2609-2613.
Ulmer et al., "Enhancement of DNA vaccine potency using conventional aluminum adjuvants". Vaccine, vol. 18, 2000, pp. 18-28.
Urasawa et al., "Sequential Passages of Human Rotavirus in MA-104 Cells". Microbiology and Immunology, vol. 25, No. 10, 1981, pp. 1025-1035.
Van Alstine, W.G., "Mystery Swine Disease in the United States". The New Pig Disease: Porcine Respiration and Reproductive Syndrome. A Report on the Seminar/Workshop Held in Brussels by the European Commission (Directorate-General for Agriculture), Apr. 29-30, 1991, pp. 65-70.
Van Alstine, W.G., "Past Diagnostic Approaches and Findings and Potentially Useful Diagnostic Strategies". Proceedings Mystery Swine Disease Committee Meeting, Oct. 6, 1990, pp. 52-58.
Van Berlo et al., "Equine Arteritis Virus-Infected Cells Contain Six Polyadenylated Virus-Specific RNAs". Virology, vol. 118, 1982, pp. 345-352.
Van Der Linden et al., "Virological kinetics and immunological responses to a porcine reproductive and respiratory syndrome virus infection of pigs at different ages". Vaccine, vol. 21, 2003, pp. 1952-1957.
Van Der Meer et al., "ORF1a-Encoded Replicase Subunits Are Involved in the Membrane Association of the Arterivirus Replication Complex". Journal of Virology, vol. 72, No. 8, 1998, pp. 6689-6698.
Van Der Most et al., "A Domain at the 3' End of the Polymerase Gene Is Essential for Encapsidation of Coronavirus Defective Interfering RNAs". Journal of Virology, vol. 65, No. 6, Jun. 1991, pp. 3219-3226.
Van Dinten et al., "An infectious arterivirus cDNA clone: Identification of a replicase point mutation that abolished discontinuous mRNA transcription". Proceedings of the National Academy of Sciences, vol. 94, Feb. 1997, pp. 997-996.
Van Dinten et al., "Processing of the Equine Arteritis Virus Replicase ORF1b Protein: Identification of Cleavage Products Containing the Putative Viral Polymerase and Helicase Domains". Journal of Virology, vol. 70, No. 10, Oct. 1996, pp. 6625-6633.
Van Dinten et al., "Proteolytic Processing of the Open Reading Frame 1b-Encoded Part of Arterivirus Replicase Is Mediated by nsp4 Serine Protease and Is Essential for Virus Replication". Journal of Virology, vol. 73, No. 3, Mar. 1999, pp. 2027-2037.
Van Marle et al., "Arterivirus discontinuous mRNA transcription is guided by base pairing between sense and antisense transcription-regulating sequences". Proceedings of the National Academy of Sciences, vol. 96, 1999, pp. 12056-12061.
Van Marle et al., "Characterization of an Equine Arteritis Virus Replicase Mutant Defective in Subgenomic mRNA Synthesis". Journal of Virology, vol. 73, No. 7, Jul. 1999, pp. 5274-5281.
Van Marle et al., "Regulation of Coronavirus mRNA Transcription". Journal of Virology, vol. 69, No. 12, Dec. 1995, pp. 7851-7856.
Van Nieuwstadt et al., "Infection with porcine respiratory coronavirus does not fully protect pigs against intestinal transmissable gastroenteritis virus". The Veterinary Record, vol. 125, No. 3, 1989, pp. 58-60.
Van Nieuwstadt et al., "Proteins Encoded by Open Reading Frames 3 and 4 of the Genome of Lelystad Virus (Arteriviridae) Are Structural Proteins of the Virion". Journal of Virology, vol. 70, No. 7, Jul. 1996, pp. 4767-4772.
Van Nieuwstadt et al., "Use of two enzyme-linked immunosorbent assays to monitor antibody responses in swine with experimentally induced infection with porcine epidemic diarrhea virus". American Journal of Veterinary Research, vol. 42, Jul. 1991, pp. 1044-1050.
Van Zijl et al., "Live Attenuated Pseudorabies Virus Expressing Envelope Glycoprotein E1 of Hog Cholera Virus Protects Swine Against Both Pseudorabies and Hog Cholera". Journal of Virology, vol. 65, No. 5, May 1991, pp. 2761-2765.
Vennema et al., "Nucleocapsid-independent assembly of coronavirus-like particles by co-expression of viral envelope protein genes". The EMBO Journal, vol. 15, No. 8, 1996, pp. 2020-2028.
Verheije et al., "Kissing Interaction between 3' Noncoding and Coding Sequences Is Essential for Porcine Arterivirus RNA Replication". Journal of Virology, vol. 76, No. 3, Feb. 2002, pp. 1521-1526.
Verheije et al., "Safety and protective efficacy of porcine reproductive and respiratory syndrome recombinant virus vaccines in young pigs". Vaccine, vol. 21, 2003, pp. 2556-2563.
Veterinary Bulletin, vol. 58, No. 11, 1988, Nos. 6903-6909, p. 932.
Veterinary Bulletin, vol. 60, No. 3, 1990, Nos. 1536-1551, pp. 255-256.
Vieira et al., "New pUC-derived cloning vectors with different selectable markers and DNA replication origins". Gene, vol. 100, 1991, pp. 189-194.
VIIIth International Symposium on Nidoviruses (Corona and Arteriviruses), May 20-25, 2000, 32 pages.
Visser, Nicolaas, "Declaration of Dr. N. Visser". Nov. 14, 1995, pp. 1-11.
Von Busse, F.W., Epidemiologic Studies on Porcine Reproductive and Respiratory Syndrome (PRRS). Tierarztliche Umschau, Dec. 1991, pp. 708-717 (Abstract in English p. 711).
Von Ohlinger et al., "Der Seuchenhafte Spatabort beim Schwein Ein Beitrag zur Atiologie des Porcine Reproductive and Respiratory Syndrome (PRRS)". Tierarztl, vol. 46, 1991, pp. 703-708.
Waltner-Toews et al., "A Field Trial to Evaluate the Efficacy of a Combined Rotavirus-Coronavirus/ Escherichia coli vaccine in Dairy Cattle"., Canadian Journal of Comparative Medicine, vol. 49, No. 1, 1985, pp. 1-9.
Wang et al., "Attenuation of porcine reproductive and respiratory syndrome virus strain MN184 using chimeric construction with vaccine sequence". Virology, vol. 371, 2008, pp. 418-429.
Ward et al., "Efficiency of human rotavirus propagation in cell culture". Journal of Clinical Microbiology, vol. 19, No. 6, Jun. 1984, pp. 748-753.
Wardley et al., "The Host Response to African Swine Fever Virus". Progress of Medical Virology, vol. 34, 1987, pp. 180-192.
Wassenaar et al., "Alternative Proteolytic Processing of the Arterivirus Replicase ORF1a Polyprotein: Evidence that NSP2 Acts as a Cofactor for the NSP4 Serine Protease". Journal of Virology, vol. 71, No. 12, Dec. 1997, pp. 9313-9322.
Webster et al., "Chemotherapy and Vaccination: a Possible Strategy for the Control of Highly Virulent Influenza Virus". Journal of Virology, vol. 55, No. 1, 1985, pp. 173-176.
Welch et al., "Construction and evaluation of genetically engineered replication-defective porcine reproductive and respiratory syndrome virus vaccine candidates". Veterinary Immunology and Immunopathology, vol. 102, 2004, pp. 277-290.
Wensvoort et al., "'Blue ear' disease in pigs". Veterinary Record, vol. 128, No. 24, Jun. 1991, p. 574.
Wensvoort et al., "'Lelystad agent'—the cause of abortus blauw (mystery swine disease)". Tijdschr Diergeneeskd, vol. 116, No. 13, Jul. 1991, pp. 675-676.
Wensvoort et al., "An Enzyme Immunoassay Employing Monoclonal Antibodies and Detecting Specifically Antibodies to Classical Swine Fever Virus". Veterinary Microbiology, vol. 17, 1988, pp. 129-140.

Gao et al., "Genomic characterization of two Chinese isolates of Porcine respiratory and reproductive syndrome virus*". Archives of Virology, vol. 149, 2004, pp. 1341-1351.
UniProt: Accession No. C9E449. "SubName: Full=M protein; SubName: Full= Membrane protein". Nov. 3, 2009.
UniProt: Accession No. D0VEE4. "SubName: Full=Unglycosylated membrane protein". Dec. 15, 2009.
UniProt: Accession No. Q6TLB4. "SubName: Full= Membrane protein M". Jul. 5, 2004.
Cano et al., "Impact of a modfied-live porcine reproductive and respiratory syndrome virus vaccine intervention on a population of pigs infected with a heterologous isolate". Vaccine, vol. 25, 2007, pp. 4382-4391.
Wesley et al., "Differentiation of a porcine reproductive and respiratory syndrome virus vaccine strain from North American field strains by restrction fragment length polymorphism analysis of ORF 5". Journal of Veterinary Diagnostic Investigation, vol. 10, 1998, pp. 140-144.
Mengeling et al., "An update of research at the National Animal Disease Center on current field strains of Porcine Reproductive and Respiratory Syndrome (PRRS) virus". Allen D. Leman Swine Conference, 1997, pp. 138-145.
Mengeling et al., "Clinical consequences of exposing pregnant gilts to strains of porcine reproductive and respiratory syndrome (PRRS) virus isolated from field cases of "atypical" PRRS". American Journal of Veterinary Research, vol. 59, No. 12, Dec. 1998, pp. 1540-1544.
Mengeling et al., "Clinical Effects of porcine reproductive and respiratory syndrome virus on pigs during the early postnatal interval". American Journal of Veterinary Research, vol. 59, No. 1, Jan. 1998, pp. 52-55.
Mengeling et al., "Comparative safety and efficacy of attenuated single-strain and multi-strain vaccines for porcine reproductive and respiratory syndrome". Veterinary Microbiology, vol. 93, 2003, pp. 25-38.
Mengeling et al., "Comparison among strains of porcine reproductive and respiratory syndrome virus for their ability to cause reproductive failure". American Journal of Veterinary Research, vol. 57, No. 6, Jun. 1996, pp. 834-839.
Mengeling et al., "Mystery Pig Disease: Evidence and Considerations for its Etiology". Proceedings of the Mystery Swine Disease Committee Meeting, Oct. 6, 1990, Denver, Colorado, Livestock Conservation Institute, Madison, WI, USA, pp. 88-90.
Mengeling et al., "Strain specificity of the immune response of pigs following vaccination with various strains of porcine reproductive and respiratory syndrome virus". Veterinary Microbiology, vol. 93, 2003, pp. 13-24.
Meredith, MJ, "Porcine Reproductive and Respiratory Syndrome (PRRS)", Pig Disease Information Center, 1st North American Edition, University of Cambridge, Aug. 1994, pp. 1-57.
Mettenleiter et al., "Isolation of a viable herpesvirus (pseudorabies virus) mutant specifically lacking all four known nonessential glycoproteins". Virology, vol. 179, No. 1, Nov. 1990, pp. 498-503.
Meulenberg et al., "An infectious cDNA clone of Porcine Reproductive and Respiratory Syndrome Virus". Coronaviruses and Arteriviruses (Advances in Experimental Medicine and Biology, vol. 440), Ch. 24, 1998, pp. 199-206.
Meulenberg et al., "Characterization of Proteins Encoded by ORFs 2 to 7 of Lelystad Virus". Virology, vol. 206, No. 1, Jan. 1995, pp. 155-163.
Meulenberg et al., "Identification and Characterization of a Sixth Structural Protein of Lelystad Virus: The Glycoprotein GP2Encoded by ORF2 Is Incorporated in Virus Particles". Virology, vol. 225, No. 1, Nov. 1996, pp. 44-51.
Meulenberg et al., "Infectious Transcripts from Cloned Genome-Length cDNA of Porcine Reproductive and Respiratory Syndrome Virus". Journal of Virology, vol. 72, No. 1, Jan. 1998, pp. 380-387.
Meulenberg et al., "Lelystad Virus, the Causative Agent of Porcine Epidemic Abortion and Respiratory Syndrome (Pears), is Related to LDV and EAV". Virology, vol. 192, 1993, pp. 62-72.
Meulenberg et al., "Localization and Fine Mapping of Antigenic Sites on the Nucleocapsid Protein N. of Porcine Reproductive and Respiratory Syndrome Virus with Monoclonal Antibodies". Virology, vol. 252, 1998, pp. 106-114.
Meulenberg et al., "Molecular characterization of Lelystad virus". Veterinary Microbiology, vol. 55, 1997, pp. 197-202.
Meulenberg et al., "Nucleocapsid Protein N. Of Lelystad Virus: Expression by Recombinant Baculovirus, Immunological Properties, and Suitability for Detection of Serum Antibodies". Clinical and Diagnostic Laboratory Immunology, vol. 2, No. 6, Nov. 1995, pp. 652-656.
Meulenberg et al., "Posttranslational Processing and Identification of a Neutralization Domain of the GP4 Protein Encoded by ORF4 of Lelystad Virus". Journal of Virology, vol. 71, No. 8, Aug. 1997, pp. 6061-6067.
Meulenberg et al., "Subgenomic RNAs of Lelystad virus contain a conserved leader-body junction sequence". Journal of General Virology, vol. 74, 1993, pp. 1697-1701.
Molenkamp et al., "Isolation and Characterization of an Arterivirus Defective Interfering RNA Genome". Journal of Virology, vol. 74, No. 7, 2000, pp. 3156-3165.
Molenkamp et al., "The arterivirus replicase is the only viral protein required for genome replication and subgenomic mRNA transcription". Journal of General Virology, vol. 81, No. 10, 2000, pp. 2491-2496.
Montagnon, B.J., "Polio and rabies vaccines produced in continuous cell lines: a reality for Vero cell line". Dev Biol Stand., vol. 70, 1989, pp. 27-47.
Moore, C., "Porcine Proliferative and Necrotyzing Pneumonia Clinical Findings". Presented at American Association of Swine Practitioners, 22nd Annual Meeting, Mar. 3-5, 1991, pp. 443-453.
Moormann et al., "Hog cholera virus: identification and characterization of the viral RNA and the virus specific RNA synthesized in infected swine kidney cells". Virus Research, vol. 11, 1988, pp. 281-291.
Moormann et al., "Molecular cloning and nucleotide sequence of hog cholera virus strain brescia and mapping of the genomic region encoding envelope protein E1". Virology, vol. 177, No. 1, Jul. 1990, pp. 184-198.
Morin et al., "Severe proliferative and necrotizing pneumonia in pigs: A newly recognized disease". Canadian Veterinary Journal, vol. 31, Dec. 1990, pp. 837-839.
Morozov et al., "Sequence analysis of open reading frames (ORFs) 2 to 4 of a U.S. isolate of porcine reproductive and respiratory syndrome virus". Archives of Virology, vol. 140, No. 7, 1995, pp. 1313-1319.
Morrison et al., "Brief Communications Serologic evidence incriminating a recently isolated virus (ATCC VR-2332) as the cause of swine infertility and respiratory syndrome (SIRS)". Journal of Veterinary Diagnostic Investigation, vol. 4, No. 2, Apr. 1992, pp. 186-188.
Morrison et al., "Sero-epidemiologic Investigation of Swine Infertility and Respiratory Syndrome (SIRS)". 72st Annual Meeting of the Conference of Research Workers in Animal Disease, Chicago, IL, Nov. 11-12, 1991, p. 55, Abstract No. 309.
Mountz et al., "The in vivo generation of murine IgD-secreting cells is accompanied by deletion of the Cμ gene and occasional deletion of the gene for the Cd1 domain". The Journal of Immunology, vol. 145, No. 5, Sep. 1990, pp. 1583-1591.
Mukamoto et al., "Immunogenicity in Aujeszky's disease virus structural glycoprotein gVI (gp50) in swine". Veterinary Microbiology, vol. 29, No. 2, Oct. 1991, pp. 109-121.
Murakami, et al., "Difference in growth behavior of human, swine, equine, and avian influenza viruses at a high temperature". Archives of Virology, vol. 100, Nos. 3-4, 1988, pp. 231-244.
Murphy et al., "Immunization Against Virus" in Virology, 2nd Edition, vol. 1, Fields, et al., eds. Raven Press, NY, 1990, pp. 469-502.
Murphy et al., "Virus Taxonomy". Chapter 2 in Fields Virology, 2nd. Edition, Fields, et al., eds, Raven Press, New York, 1990, pp. 9-35.
Murtaugh et al., "Comparison of the structural protein coding sequences of the VR-2332 and Lelystad virus strains of the PRRS virus". Archives of Virology, vol. 140, No. 8, 1995, pp. 1451-1460.

Murtaugh et al., "Genetic Variation in the PRRS Virus". Coronaviruses and Arteriviruses, Plenum Press, New York, 1998, pp. 787-794.
Murtaugh et al., "Immunological Responses of Swine to Porcine Reproductive and Respiratory Syndrome Virus Infection". Viral Immunology, vol. 15, No. 4, 2002, pp. 533-547.
Murtaugh et al., "Role of Viral Proteases in PRRS Immunity, Project Period Sep. 1, 1997-Dec. 31, 2002, no cost extension Jan. 1, 2003-Jun. 30, 2003". Final Report: Aug. 30, 2003, Department of Veterinary Pathology, University of Minnesota, St. Paul, MN and Boehringer Ingelheim Vetmedica, Inc., Ames, IA, 2003, pp. 1-38.
Murtaugh, "Allen D Lehman Swine Conference: the Evolution of the Swine veterinary profession: The PRRS Virus". University of Minnesota, Veterinary Continuing Education and Extension, vol. 20, 1993, pp. 43-47.
Myers et al., "Propagation of avian rotavirus in primary chick kidney cell and MA104 cell cultures". Avian Diseases, vol. 33, No. 3, Jul.-Sep. 1989, pp. 578-581.
Nakamura et al., "Studies on Swine Influenza III. Propagation of Swine Influenza Virus in Explants of Respiratory Tract Tissues from Fetal Pigs". The Cornell Veterinarian, vol. LX, No. 1, Jan. 1970, pp. 27-35.
Narayanan et al., "Characterization of the Coronavirus M Protein and Nucleocapsid Interaction in Infected Cells". Journal of Virology, vol. 74, No. 17, Sep. 2000, pp. 8127-8134.
NCBI: Accession No. AE005172. "Arabidopsis thaliana chromosome 1, top arm complete sequence." Dec. 14, 2000.
NCBI: Accession No. AF046869. "Porcine reproductive and respiratory syndrome virus isolate 16244B, Feb. 18, 1997 (Nebraska) pass.3, complete genome." Mar. 17, 1999.
NCBI: Accession No. AF066183. "Porcine reproductive and respiratory syndrome virus RespPRRS MLV, complete genome." Feb. 22, 2001.
NCBI: Accession No. AF159149. "Porcine reproductive and respiratory syndrome virus isolate MLV RespPRRS/Repro, complete genome." Aug. 28, 2000.
NCBI: Accession No. AF176348. "Porcine reproductive and respiratory syndrome virus isolate PA8 complete genome." Sep. 3, 2002.
NCBI: Accession No. AF184212. "Porcine reproductive and respiratory syndrome virus strain SP, complete genome." Sep. 28, 2000.
NCBI: Accession No. AF325691. "Porcine reproductive and respiratory syndrome virus isolate NVSL 977985 IA 1-4-2, complete genome." Feb. 11, 2001.
NCBI: Accession No. AF331831. "Porcine reproductive and respiratory syndrome virus BJ-4, complete genome." Jan. 15, 2001.
NCBI: Accession No. M96262. "Lelystad virus, complete genome." Nov. 8, 2000.
NCBI: Accession No. M96262.2. "Lelystad virus, complete genome." Nov. 8, 2000.
NCBI: Accession No. NC_001639. Lactate dehydrogenase-elevating virus, complete genome. Dec. 8, 2008.
NCBI: Accession No. NC_001961. "Porcine reproductive and respiratory syndrome virus, complete genome." Jan. 12, 2004.
NCBI: Accession No. NC_002533. "Lelystad virus, complete genome." Nov. 11, 2000.
NCBI: Accession No. NC_002534. "Lactate dehydrogenase-elevating virus, complete genome." Dec. 29, 2003.
NCBI: Accession No. U15146. "Lactate dehydrogenase-elevating virus Plagemann strain, complete genome." Jan. 26, 1996.
NCBI: Accession No. U87392 AF030244 000153. "Porcine reproductive and respiratory syndrome virus strain VR-2332, complete genome." Nov. 17, 2000.
Nelsen et al., "Porcine Reproductive and Respiratory Syndrome Virus Comparison: Divergent Evolution on Two Continents". Journal of Virology, vol. 73, No. 1, Jan. 1999, pp. 270-280.
Nelson et al., "Differentiation of U.S. And European Isolates of Porcine Reproductive and Respiratory Syndrome Virus by Monoclonal Antibodies". Journal of Clinical Microbiology, vol. 31, No. 12, Dec. 1993, pp. 3184-3189.
Nelson et al., "High affinity interaction between nucleocapsid protein and leader/intergenic sequence of mouse hepatitis virus RNA". Journal of General Virology, vol. 81, 2000, pp. 181-188.
Nielsen et al., "Generation of an Infectious Clone of VR-2332, a Highly Virulent North American-Type Isolate of Porcine Reproductive and Respiratory Syndrome Virus". Journal of Virology, vol. 77, No. 6, Mar. 2003, pp. 3702-3711.
Nishimura et al., "Replication and Synthesis of Japanese Encephalitis Virus Ribonucleic Acids in Vero Cells". Japanese Journal of Microbiology, vol. 15, No. 4, 1971, pp. 309-316.
Nodelijk et al., "A quantitative assessment of the effectiveness of PRRSV vaccination in pigs under experimental conditions". Vaccine, vol. 19, 2000, pp. 3636-3644.
Notice of Opposition by Akzo Nobel against European Patent No. 0 587 780, Nov. 28, 1995, EP.
Notice of Opposition by Cyanamid Iberica against European Patent No. 0 587 780, Nov. 28, 1995, EP.
Nuttall, P.A., "Growth Characteristics of Two Strains of Bovine Virus Diarrhoea Virus". Archives of Virology, vol. 66, 1980, pp. 365-369.
Oirschot et al., "Development of an Elisa for detection of antibodies to glycoprotein I of Aujeszky's disease virus: a method for the serological differentiation between infected and vaccinated pigs". Journal of Virological Methods, vol. 22, 1988, pp. 191-206.
Ojeh et al., "Isolation, characterisation and serial propagation of a Nigerian strain of porcine group A rotavirus in a monkey kidney cell line (MA104)". Discovery and Innovation, vol. 8, No. 2, Jun. 1996, pp. 159-164.
Oleksiewicz et al., "Epitope Mapping Porcine Reproductive and Respiratory Syndrome Virus by Phage Display: the nsp2 Fragment of the Replicase Polyprotein Contains a Cluster of B-Cell Epitopes". Journal of Virology, vol. 75, No. 7, Apr. 2001, pp. 3277-3290.
Oleksiewicz et al., "Semen from Boars Infected with Porcine Reproductive and Respiratory Syndrome Virus (PRRSV) Contains Antibodies Against Structural as Well as Nonstructural Viral Proteins". Veterinary Microbiology, vol. 81, 2001, pp. 109-125.
Olsthoorn et al., "A conformational switch at the 3' end of a plant virus RNA regulates viral replication". The EMBO Journal, vol. 18, No. 17, 1999, pp. 4856-4864.
Opriessnig et al., "Comparison of Molecular and Biological Characteristics of a Modified Live Porcine Reproductive and Respiratory Syndrome Virus (PRRSV) Vaccine (Ingelvac PRRS MLV), the Parent Strain of the Vaccine (ATCC VR2332), ATCC VR2385, and Two Recent Field Isolates of PRRSV". Journal of Virology, vol. 76, No. 23, Dec. 2002, pp. 11837-11844.
Opriessnig et al., "Use of an Experimental Model to Test the Efficacy of Planned Exposure to Live Porcine Reproductive and Respiratory Syndrome Virus". Clinical and Vaccine Immunology, vol. 14, No. 12, Dec. 2007, pp. 1572-1577.
Ostrowski et al., "Identification of Neutralizing and Nonneutralizing Epitopes in the Porcine Reproductive and Respiratory Syndrome Virus GP5 Ectodomain". Journal of Virology, vol. 76, No. 9, May 2002, pp. 4241-4250.
Pan et al., "Replication of African swine fever virus in cell cultures". American Journal of Veterinary Research, vol. 41, No. 9, Sep. 1980, pp. 1357-1367.
Parratt et al., "Radioimmunoassay of Antibody and its Clinical Applications". John Wiley & Sons, Chichester, 1982, p. 43.
Parsley et al., "Poly (rC) binding protein 2 forms a ternary complex with the 5'-terminal sequences of poliovirus RNA and the viral 3CD proteinase". RNA, vol. 3, 1997, pp. 1124-1134.
Patriarca, et al., "Lack of Significant Person-to-Person Spread of Swine Influenza-Like Virus Following Fatal Infection in an Immunocomprised Child". American Journal of Epidemiology, vol. 119, No. 2, 1984, pp. 152-158.
Paul et al., "Porcine Reproductive and Respiratory Syndrome: An Overview". Journal of Clinical Veterinary Medicine, vol. 11, No. 12, Nov. 1993, pp. 1-16.
Pearson et al., "Improved tools for biological sequence comparison". Proceedings of the National Academy of Sciences, vol. 85, Apr. 1988, pp. 2444-2448.
Pedersen et al., "Open Reading Frame 1a-Encoded Subunits of the Arterivirus Replicase Induce Endoplasmic Reticulum-Derived Double-Membrane Vesicles Which Carry the Viral Replication Complex". Journal of Virology, vol. 73, No. 3, Mar. 1999, pp. 2016-2026.

Pejsak et al., "Clinical signs and economic losses caused by porcine reproductive and respiratory syndrome virus in a large breeding farm". Veterinary Microbiology, vol. 44, 1997, pp. 317-322.
Peng et al., "Analysis of Second-Site Revertants of a Murine Coronavirus Nucleocapsid Protein Deletion Mutant and Construction of Nucleocapsid Protein Mutants by Targeted Rna Recombination". Journal of Virology, vol. 69, No. 6, Jun. 1995, pp. 3449-3457.
Penzes et al., "Characterization of a Replicating and Packaged Defective RNA of Avian Coronavirus Infectious Bronchitis Virus". vol. 203, No. 2, Sep. 1994, pp. 286-293.
Percy et al., "Expression of a Foreign Protein by Influenza a Virus". Journal of Virology, vol. 68, No. 7, Jul. 1994, pp. 4486-4492.
Pirtle et al., "Morphologic Heterogeneity of a Strain of Swine Influenza Virus (A/Swine/Wisconsin/1/68, Hsw1N1) Propagated at Different Temperatures". American Journal of Veterinary Research, vol. 36, No. 1, 1975, pp. 1783-1787.
Plagemann et al., "Lactate Dehydrogenase-Elevating Virus, Equine Arteritis Virus, and Simina Hemorrhagic Fever Virus: A New Group of Positive-Strand RNA Viruses". Advances in Virus Research, vol. 41, 1991, pp. 99-192.
Pol et al., "Pathological, ultrastructural, immunohistochemical changes caused by Lelystad virus in experimentally induced infections of mystery swine disease (synonym: porcine epidemic abortion and respiratory syndrome (Pears))". Veterinary Quarterly, vol. 13, No. 3, Jul. 1991, pp. 137-143.
Polson et al., "An evaluation of the financial impact of Porcine Reproductive and Respiratory Syndrome (PRRS) in nursery pigs". Proceedings of the 13th International Pig Veterinary Society Congress, Jun. 1994, p. 31.
Polson et al., "Financial Implications of Mystery Swine Disease (MSD)". 1993, pp. 8-28.
Polson, DD, "Answers to Your Questions on PRRS". NOBL Laboratories, 1993, 18 pages.
Polson, DD, "RespPRRS a PRRS Vaccine Review", NOBL Laboratories, 1993, 22 pages.
Porcine Reproductive and Respiratory Syndrome: A Report on the Seminar Held in Brussels on Nov. 4-5, 1991 and Organized by the European Commission.
Poser, C.M., "Swine Influenza Vaccination: Truth and Consequences". Archives of Neurology, vol. 42, No. 11, 1985, pp. 1090-1092.
Potgieter et al., "Isolation of Swine Influenza Virus in Oklahoma". Journal of the American Veterinary Medical Association, vol. 171, No. 8, 1977, pp. 758-760.
Potts et al., "Peroxidase-labeled primary antibody method for detection of pestivirus contamination in cell cultures". Journal of Virological Methods, vol. 26, No. 1, Oct. 1989, pp. 119-124.
Quaife, T. "Mystery Agent Isolated! Isolation of the etiological agent behind mystery swine disease is a major breakthrough". Swine Practitioner, Mystery Disease: Part 8, Nov. 1991, pp. 4-7.
Reed et al., "A Simple Method of Estimating Fifty Per Cent Endpoints"., The American Journal of Hygiene, vol. 27, No. 3, May 1938, pp. 493-497.
Reed et al., "Persistent Respiratory Virus Infection in Tracheal Organ Cultures". British Journal of Experimental Pathology, vol. 50, 1969, pp. 378-388.
"Dutch Team Isolates Mystery Pig Disease Agent", Animal Pharm, vol. 230, Abstract No. 00278268, Jun. 21, 1991, p. 21.
"For purification of viral RNA from Plasma, Serum, Cell-free body fluids, Cell-Culture supernatants". QIAamp® Viral RNA Mini Kit Handbook, QIAGEN, Jan. 1999, Cat #52906, pp. 1-35.
"Frontiers closing to mystery disease pigs". Animal Pharm., No. 228, May 24, 1991, p. 2.
"Revision of the taxonomy of the Coronavirus, Torovirus, and Arterivirus genera". Archives of Virology, vol. 135, 1994, pp. 227-239.
Abstracts of Papers Presented at the 71st Annual Meeting of the Conference of Research Workers in Animal Disease, Nos. 1-6, Nov. 5-6, 1990, 2 pages.
Aksenova et al., "Cultivation of the rabies virus in the continuous kidney cell line 4647 from the green marmoset". Vopr. Virusol., vol. 30, No. 2, 1985, pp. 180-182. (See AXEOVA for English Abstract).
Albina et al., "Immune responses in pigs infected with porcine reproductive and respiratory syndrome virus (PRRSV)". Veterinary Immunology and Immunopathology, vol. 61, 1998, pp. 49-66.
Allan et al., "Experimental infection of colostrum deprived piglets with porcine circovirus 2 (PCV2) and procine reproductive and respiratory syndrome virus (PRRSV) potentiates PCV2 replication". 2000, Archives of Virology, vol. 145, pp. 2421-2429.
Allende et al., "Mutations in the genome of porcine reproductive and respiratory syndrome virus responsible for the attenuated phenotype". Archives of Virology, vol. 145, No. 6, Jun. 2000, pp. 1149-1161.
Allende et al., "North American and European porcine reproductive and respiratory syndrome viruses differ in nonstructural protein coding regions". Journal of General Virology, vol. 80, 1999, pp. 307-315.
Altschul et al., "Basic Local Alignment Search Tool". Journal of Molecular Biology, vol. 215, 1990, pp. 403-410.
Andreyev et al., "Genetic variation and phylogenetic relationships of 22 porcine reproductive and respiratory syndrome virus (PRRSV) field strains based on sequence analysis of open reading frame 5". Archives of Virology, vol. 142, 1997, pp. 993-1001.
Ashworth et al., "Antibody-dependent cell-mediated cytotoxicity (ADCC) in Aujeszky's disease". Archives of Virology, vol. 59, No. 4, 1979, pp. 307-318.
Axenova, T.A. "Propagation of Rabies Vaccine Virus in Continuous Green Monkey Kidney Cells 4647". Vopr. Virusol., vol. 30, No. 2, 1985, p. 182. (English Abstract of AKSENOVA Reference.).
Backstrom et al., "Respiratory Diseases of Swine". Veterinary Clinics of North America: Large Animal Practice, vol. 4, No. 2, Nov. 1982, pp. 259-276.
Barfoed et al., "DNA vaccination of pigs with open reading frame 1-7 of PRRS virus". Vaccine, vol. 22, 2004, pp. 3628-3641.
Baric et al., "Interactions between Coronavirus Nucleocapsid Protein and Viral RNAs: Implications for Viral Transcription". Journal of Virology, vol. 62, No. 11, Nov. 1988, pp. 4280-4287.
Baric et al., "Subgenomic Negative-Strand RNA Function during Mouse Hepatitis Virus Infection". Journal of Virology, vol. 74, No. 9, May 2000, pp. 4039-4046.
Bautista et al., "Comparison of Porcine Alveolar Macrophages and CL 2621 for the Detection of Porcine Reproductive and Respiratory Syndrome (PRRS) Virus and Anti-PRRS Antibody". Journal of Veterinary Diagnostic Investigation, vol. 5, No. 2, Apr. 1993, pp. 163-165.
Bautista et al., "Serologic Survey for Lelystad and VR-2332 Strains of Porcine Respiratory and Reproductive Syndrome (PRRS) Virus in US Swine Herds". Journal of Veterinary Diagnostic Investigation, vol. 5, No. 4, Oct. 1992, pp. 612-614.
Beale, AJ, "Vaccines and antiviral drugs". Principles of bacteriology, virology and immunity, vol. 3, Ch. 86, 1984, pp. 147-161.
Beare et al., "Further Studies in Man of Man of HSw1N1 Influenza Viruses". Journal of Medical Virology, vol. 5, 1980, pp. 33-38.
Beghi et al., "Guillain-Barré Syndrome: Clinicoepidemiologic Features and Effect of Influenza Vaccine". Archives of Neurology, vol. 42, No. 11, 1985, pp. 1053-1057.
Benfield et al., "Characterization of swine infertility and respiratory syndrome (SIRS) virus (isolate ATCC VR-2332)". Journal of Veterinary Diagnostic Investigation, vol. 4, 1992, pp. 127-133.
Benfield et al., "Etiologic Agent of Swine Infertility and Respiratory Syndrome in the United States". 72st Annual Meeting of the Conference of Research Workers in Animal Disease, Chicago, IL, Nov. 11-12, 1991, p. 48, Abstract No. 268.
Benfield et al., "Properties of SIRS Virus Isolate ATCC VR-2332 in the United States and Preliminary Characterization of a Monoclonal Antibody to this Virus". American Association of Swine Practitioners Newsletter, vol. 4, No. 4, Jul./Aug. 1992, pp. 19-21.
Berendt et al., "Evaluation of Commercially Prepared Vaccines for Experimentally Induced Type/A/New Jersey/8/76 Influenza Virus Infections in Mice and Squirrel Monkeys". The Journal of Infectious Diseases, vol. 136, Dec. 1977, pp. S712-S718.
Berendt et al., "Reaction of Squirrel Monkeys to Intratracheal Inoculation with Influenza/A/New Jersey/76 (Swine) Virus". Infection and Immunity, vol. 16, No. 2, May 1977, pp. 476-479.
Bilodeau et al., "'Porcine Reproductive and Respiratory Syndrome' in Quebec". The Veterinary Record, Aug. 3, 1991, p. 102.

Blackburn et al., "Use of human influenza vaccine to protect against blue-eared pig disease". Veterinary Record, vol. 129, No. 1, Jul. 1991, p. 19.
Bohl et al., "Isolation and Serotyping of Porcine Rotaviruses and Antigenic Comparison with Other Rotaviruses". Journal of Clinical Microbiology, vol. 19, No. 2, Feb. 1984, pp. 105-111.
Bouillant et al., "Viral Susceptibility of a Cell Line Derived from the Pig Oviduct". Canadian Journal of Comparative Medicine, vol. 39, 1975, pp. 450-456.
Boursnell et al., "Sequence of the membrane protein gene from avian coronavirus IBV". Virus Research, vol. 1, 1984, pp. 303-313.
Boursnell et all., "Completion of the Sequence of the Genome of the Coronavirus Avian Infectious Bronchitis Virus". Journal of General Virology, vol. 68, 1987, pp. 57-77.
Bowie et al., "Deciphering the Message of Protein Sequences: Tolerance to Amino Acid Substitutions". Science, vol. 247, 1990, pp. 1306-1310.
Boyer et al., "Infectious Transcripts and cDNA Clones of RNA Viruses". Virology, vol. 198, No. 2, Feb. 1994, pp. 415-426.
Bramel-Verheije et al., "Expression of a Foreign Epitope by Porcine Reproductive and Respiratory Syndrome Virus". Virology, vol. 278, 2000, pp. 380-389.
Bredenbeek et al., "The primary structure and expression of the second open reading frame of the polymerase gene of the coronavirus MHV-A59; a highly conserved polymerase is expressed by an efficient ribosomal frameshifting mechanism". Nucleic Acids Research, vol. 18, No. 7, 1990, pp. 1825-1832.
Brenner et al., "A Negative Staining Method for High Resolution Electron Microscopy of Viruses". Biochimica Et Biophysica Acta, vol. 34, 1959, pp. 103-110.
Brinton-Darnell et al., "Structure and chemical-physical characteristics of lactate dehydrogenase-elevating virus and its RNA". Journal of Virology, vol. 16, No. 2, Aug. 1975, pp. 420-433.
Brinton-Darnell, M. "Lactate Dehydrogenase-Elevating, Equine Arteritis and Lelystad Viruses". Encyclopedia of Virology, vol. 2, 1999, pp. 763-771.
Bruner, D.W., "Table XXXII. Characteristics of Viral Respiratory Infections in Swine" Hagan's Infectious Diseases of Domestic Animals: With Special Reference to Etiology, Diagnosis, and Biologic Therapy, Sixth Edition, Comstock Publishing Associations, a division of Cornell University Press, Ithaca and London, 1973, 5 pages.
Brüggemann et al., "Immunoglobulin V region variants in hybridoma cells. I. Isolation of a variant with altered idiotypic and antigen binding specificity". The EMBO Journal, vol. 1, No. 5, 1982, pp. 629-634.
Buck, K. W., "Comparison of the Replication of Positive-Stranded RNA Viruses of Plants and Animals". Advances in Virus Research, vol. 47, 1996, pp. 159-251.
Burgess et al., "Possible Dissociation of the Heparin-binding and Mitogenic Activities of Heparin-binding (Acidic Fibroblast) Growth Factor-1 from Its Receptor-binding Activities by Site-directed Mutagenesis of a Single Lysine Residue". The Journal of Cell Biology, vol. 111, 1990, pp. 2129-2138.
Burroughs, et al., "Relationship of San Miguel Sea Lion Virus to Other Members of the Calicivirus Group". Intervirology, vol. 10, 1978, pp. 51-59.
Cabasso et al., "Propagation of Infectious Canine Hepatitis Virus in Tissue Culture". Proceedings of the Society for Experimental Biology and Medicine, vol. 85, 1954, pp. 239-245.
Caeiro et al., "In vitro DNA replication by cytoplasmic extracts from cells infected with African swine fever virus". Virology, vol. 179, No. 1, Nov. 1990, pp. 87-94.
Callebaut et al., "Antigenic Differentiation between Transmissible Gastroenteritis Virus of Swine and a Related Porcine Respiratory Coronavirus". Journal of General Virology, vol. 69, 1988, pp. 1725-1730.
Carrascosa et al., "Relationship of San Miguel Sea Lion Virus to Other Members of the Calicivirus Group". Journal of Virological Methods, vol. 3, No. 6, Jan. 1982, pp. 303-310.
Knowles et al., "Classification of porcine enteroviruses by antigenic analysis and cytopathic effects in tissue culture: Description of 3 new serotypes". Archives of Virology, vol. 62, No. 3, 1979, pp. 201-208.
Kolodziej et al., "Epitope tagging and protein surveillance". Methods in Enzymology, vol. 194, 1991, pp. 508-519.
Kouvelos et al., "Comparison of Bovine, Simian and Human Rotavirus Structural Glycoproteins". Journal of General Virology, vol. 65, Jul. 1984, pp. 1211-1214.
Kreutz, L.C., "Cellular membrane factors are the major determinants of porcine reproductive and respiratory syndrome virus tropism". Virus Research, vol. 53, 1998, pp. 121-128.
Kundin, W.D., "Hong Kong A-2 Influenza Virus Infection among Swine during a Human Epidemic in Taiwan". Nature, vol. 228, Nov. 1970, p. 857.
Kuo et al., "A Nested Set of Eight RNAs Is Formed in Macrophages Infected with Lactate Dehydrogenase-Elevating Virus", Journal of Virology, vol. 65, No. 9, Sep. 1991, pp. 5118-5123.
Kusanagi et al., "Isolation and Serial Propagation of Porcine Epidemic Diarrhea Virus in Cell Cultures and Partial Characterization of the Isolate". Journal of Veterinary Medical Science, vol. 54, No. 2, 1992, pp. 313-318.
Kutsuzawa et al., "Isolation of Human Rotavirus Subgroups 1 and 2 in Cell Culture". Journal of Clinical Microbiology, vol. 16, No. 4, Oct. 1982, pp. 727-730.
Kwang et al., "Cloning, expression, and sequence analysis of the ORF4 gene of the porcine reproductive and respiratory syndrome virus MN-1b". Journal of Veterinary Diagnostic Investigation, vol. 6, No. 3, Jul. 1994, pp. 293-296.
Labarque et al., "Effect of cellular changes and onset of humoral immunity on the replication of porcine reproductive and respiratory syndrome virus in the lungs of pigs". Journal of General Virology, vol. 81, 2000, pp. 1327-1334.
Labarque et al., "Respiratory tract protection upon challenge of pigs vaccinated with attenuated porcine reproductive and respiratory syndrome virus vaccines". Veterinary Microbiology, vol. 95, 2003, pp. 187-197.
Lai et al., "Coronavirus: how a large RNA viral genome is replicated and transcribed". Infectious Agents and Disease, vol. 3, Nos. 2-3, 1994, pp. 98-105.
Lai et al., "Coronavirus: organization, replication and expression of genome". Annual Review of Microbiology, vol. 33, 1990, pp. 303-333.
Lai et al., "Infectious RNA transcribed from stably cloned full-length cDNA of dengue type 4 virus". Proceedings of the National Academy of Sciences, vol. 88, Jun. 1991, pp. 5139-5143.
Lazar et al. "Transforming Growth Factor a: Mutation of Aspartic Acid 47 and Leucine 48 Results in Different . Biological Activities". Molecular and Cellular Biology, vol. 8, No. 3, Mar. 1988, pp. 1247-1252.
Leitner et al., "DNA and RNA-based vaccines: principles, progress and prospects". Vaccine, vol. 18, 2000, pp. 765-777.
Levy et al., "Freeze-drying is an effective method for preserving infectious type C retroviruses". Journal of Virological Methods, vol. 5, Nos. 3-4, Nov. 1982, pp-165-171.
Liljestrom et al., "A New Generation of Animal Cell Expression Vectors Based on the Semliki Forest Virus Replicon". Nature Biotechnology, vol. 9, 1991, pp. 1356-1361.
Lin et al., "Deletion Mapping of a Mouse Hepatitis Virus Defective Interfering RNA Reveals the Requirement of an Internal and Discontiguous Sequence fro Replication". Journal of Virology, vol. 67, No. 10, Oct. 1993, pp. 6110-6118.
Lin et al., "Identification of the cis-Acting Signal for Minus-Strand RNA Synthesis of a Murine Coronavirus: Implications for the Role of Minus-Strand RNA in RNA Replication and Transcription". Journal of Virology, vol. 68, No. 12, Dec. 1994, pp. 8131-8140.
Lin et al., "The 3' Untranslated Region of Coronavirus RNA Is Required for Subgenomic mRNA Transcription from a Defective Interfering RNA". Journal of Virology, vol. 70, No. 10, Oct. 1995, pp. 7236-7240.
Liu et al., "A Specific Host Cellular Protein Binding Element Near the 3? End of Mouse Hepatitis Virus Genomic RNA". Virology, vol. 232, No. 1, May 1997, pp. 74-85.
Loula, T., "Clinical Presentation of Mystery Pig Disease in the Breeding Herd and Suckling Piglets". Proceedings of the Mystery Swine Disease Committee Meeting, Denver, CO, Oct. 6, 1990, pp. 37-40.

Loula, T., "Mystery Pig Disease", Agri-Practice, vol. 12, No. 1, Jan.-Feb. 1991, pp. 29-34.
Luytjes et al., "Replication of Synthetic Defective Interfering RNAs Derived from Coronavirus Mouse Hepatitis Virus-A59". Virology, vol. 216, No. 1, Feb. 1996, pp. 174-183.
LV et al., "An infectious cDNA clone of a highly pathogenic porcine reproductive and respiratory syndrome virus variant associated with porcine high fever syndrome". Journal of General Virology, vol. 89, 2008, pp. 2075-2079.
Madec et al., "Consequences pathologiques d'un episode grippal severe (virus swine A/H1N1 dans les conditions naturelles chez la truie non immune en debut de gestation". Comparative Immunology, Microbiology and Infectious Diseases, vol. 12, Nos. 1-2, 1989, pp. 17-27.
Madin, S.H. "Vesicular Exanthema Virus". Virus Infections of Porcines, Elsevier Science Publishers B.V., 1989, pp. 267-271.
Makabe et al., "Hemagglutination with Ovine Rotavirus". Archives of Virology, vol. 90, 1986, pp. 153-158.
Makino et al., "Leader sequences of murine coronavirus mRNAs can be freely reassorted: Evidence for the role of free leader RNA in transcription". Proceedings of the National Academy of Sciences, vol. 83, Jun. 1986, pp. 4204-4208.
Makino et al., "Primary Structure and Translation of a Defective Interfering RNA of Murine Coronavirus". Virology, vol. 166, 1988, pp. 550-560.
Mardassi et al., "Identification of major differences in the nucleocapsid protein genes of a Québec strain and European strains of porcine reproductive and respiratory syndrome virus". vol. 75, No. 3, Mar. 1994, pp. 681-685.
Mardassi et al., "Molecular analysis of the ORFs 3 to 7 of porcine reproductive and respiratory syndrome virus, Québec reference strain". Archives of Virology, vol. 140, No. 8, 1995, pp. 1405-1418.
Mason, P.W., "Maturation of Japanese encephalitis virus glycoproteins produced by infected mammalian and mosquito cells". Virology, vol. 169, No. 2, Apr. 1989, pp. 354-364.
Masters et al., "Functions of the coronavirus nucleocapsid protein". Coronaviruses and Their Diseases, Plenum Press, New York, pp. 235-238.
Masurel, N., "Swine Influenza Virus and the Recycling of Influenza-A Viruses in Man". The Lancet, Jul. 31, 1976, pp. 244-247.
McAuliffe et al., "Codon Substitution Mutations at Two Positions in the L Polymerase Protein of Human Parainfluenza Virus Type 1 Yield Viruses with a Spectrum of Attenuation in Vivo and Increased Phenotypic Stability in Vitro". Journal of Virology, vol. 78, No. 4, Feb. 2004, pp. 2029-2036.
McCullough et al., "9. Experimental Transmission of Mystery Swine Disease", The New Pig Disease Porcine Respiration and Reproductive Syndrome, A report on the seminar/workshop held in Brussels on Apr. 29-30, 1991, pp. 46-52.
McDaniel, H.A., "African Swine Fever". Diseases of Swine, 5th Edition, Chapter 18, The Iowa State University Press, Ames, Iowa, 1981, pp. 237-245.
McFerran, J.B., "Reovirus Infection". Diseases of Swine, Fifth Edition, Chapter 28, The Iowa State University Press, Ames, Iowa, 1981, pp. 330-334.
McIntosh, "Diagnostic Virology". Fields Virology, Ch. 17, Second Edition, vol. 1, 1990, pp. 411-437.
McKinney, W.P., "Fatal Swine Influenza Pneumonia During Late Pregnancy". Archives of Internal Medicine, vol. 150, No. 1, Jan. 1990, pp. 213-215.
McQueen et al., "Influenza in animals". Advances in Veterinary Science, vol. 12, 1968, pp. 285-336.
Meikeljohn et al., "Respiratory Virus Vaccine Evaluation and Surveillance". Semi-Annual Contract Progress Report to the National Institute of Allergy and Infectious Diseases, Sep. 15, 1965 to Mar. 15, 1966, 21 pgs.
Melchers et al., "Cross-talk between orientation-dependent recognition determinants of a complex control RNA element, the enterovirus oriR". RNA, vol. 6, 2000, pp. 976-987.
Mendez et al., "Molecular Characterization of Transmissible Gastroenteritis Coronavirus Defective Interfering Genomes: Packaging and Heterogeneity". Virology, vol. 217, 1996, pp. 495-507.
Meng et al., "Characterization of a High-Virulence US Isolate of Porcine Reproductive and Respiratory Syndrome Virus in a Continuous Cell Line, ATCC CRL11171". Journal of Veterinary Diagnostic Investigation, vol. 8, No. 3, Jul. 1996, pp. 374-381.
Meng et al., "Molecular cloning and nucleotide sequencing of the '-terminal genomic RNA of the porcine reproductive and respiratory syndrome virus". Journal of General Virology, vol. 75, 1994, pp. 1795-1801.
Meng et al., "Phylogenetic analyses of the putative M (ORF 6) and N (ORE 7) genes of porcine reproductive and respiratory syndrome virus (PRRSV): implication for the existence of two genotypes of PRRSV in the U.S.A. and Europe". Archives of Virology, vol. 140, No. 4, 1995, pp. 745-755.
Meng, X.J., "Heterogeneity of porcine reproductive and respiratory syndrome virus: implications for current vaccine efficacy and future vaccine development". Veterinary Microbiology, vol. 74, 2000, pp. 309-329.

* cited by examiner

SEQUENCE LISTING

```
<160> NUMBER OF SEQ ID NOS: 23

<210> SEQ ID NO 1
<211> LENGTH: 20
<212> TYPE: DNA
<213> ORGANISM: Lelystad virus
<220> FEATURE:
<221> NAME/KEY: primer_bind
<222> LOCATION: (1)..(20)
<223> OTHER INFORMATION: /note="Primer 11U113"

<400> SEQUENCE: 1

tacaggtgcc tgatccaaga                                          20


<210> SEQ ID NO 2
<211> LENGTH: 30
<212> TYPE: DNA
<213> ORGANISM: Lelystad virus
<220> FEATURE:
<221> NAME/KEY: primer_bind
<222> LOCATION: (1)..(30)
<223> OTHER INFORMATION: /note="Anchor primer ALG3"

<400> SEQUENCE: 2

cacgaattca ctatcgattc tggatccttc                               30


<210> SEQ ID NO 3
<211> LENGTH: 31
<212> TYPE: DNA
<213> ORGANISM: Lelystad virus
<220> FEATURE:
<221> NAME/KEY: primer_bind
<222> LOCATION: (1)..(31)
<223> OTHER INFORMATION: /note="Primer LV69"

<400> SEQUENCE: 3

aggtcgtcga cgggccccgt gatcgggtac c                             31


<210> SEQ ID NO 4
<211> LENGTH: 20
<212> TYPE: DNA
<213> ORGANISM: Lelystad virus
<220> FEATURE:
<221> NAME/KEY: primer_bind
<222> LOCATION: (1)..(20)
<223> OTHER INFORMATION: /note="Primer ALG4"
```

<400> SEQUENCE: 4
gaaggatcca gaatcgatag 20

<210> SEQ ID NO 5
<211> LENGTH: 22
<212> TYPE: DNA
<213> ORGANISM: Lelystad virus
<220> FEATURE:
<221> NAME/KEY: primer_bind
<222> LOCATION: (1)..(22)
<223> OTHER INFORMATION: /note="Primer LV76"

<400> SEQUENCE: 5
tctaggaatt ctagacgatc gt 22

<210> SEQ ID NO 6
<211> LENGTH: 22
<212> TYPE: DNA
<213> ORGANISM: Lelystad virus
<220> FEATURE:
<221> NAME/KEY: primer_bind
<222> LOCATION: (1)..(22)
<223> OTHER INFORMATION: /note="Primer LV75"

<400> SEQUENCE: 6
tctaggaatt ctagacgatc gt 22

<210> SEQ ID NO 7
<211> LENGTH: 20
<212> TYPE: DNA
<213> ORGANISM: Lelystad virus
<220> FEATURE:
<221> NAME/KEY: primer_bind
<222> LOCATION: (1)..(20)
<223> OTHER INFORMATION: /note="Sense primer 39U70R"

<400> SEQUENCE: 7
ggagtggtta acctcgtcaa 20

<210> SEQ ID NO 8
<211> LENGTH: 33
<212> TYPE: DNA
<213> ORGANISM: Lelystad virus
<220> FEATURE:
<221> NAME/KEY: primer_bind
<222> LOCATION: (1)..(33)
<223> OTHER INFORMATION: /note="Sense primer LV59"

<400> SEQUENCE: 8
tcggaatcta gatctcacgt ggtgcagctg ctg 33

<210> SEQ ID NO 9
<211> LENGTH: 20
<212> TYPE: DNA
<213> ORGANISM: Lelystad virus
<220> FEATURE:
<221> NAME/KEY: primer_bind
<222> LOCATION: (1)..(20)
<223> OTHER INFORMATION: /note="Antisense primer 61U303"

<400> SEQUENCE: 9
catcaacacc tgtgcagacc 20

<210> SEQ ID NO 10
<211> LENGTH: 20
<212> TYPE: DNA
<213> ORGANISM: Lelystad virus -continued
<220> FEATURE:
<221> NAME/KEY: primer_bind
<222> LOCATION: (1)..(20)
<223> OTHER INFORMATION: /note="Sense primer 61U526R"

<400> SEQUENCE: 10
ttccttctct ggcgcatgat 20

<210> SEQ ID NO 11
<211> LENGTH: 30
<212> TYPE: DNA
<213> ORGANISM: Lelystad virus
<220> FEATURE:
<221> NAME/KEY: primer_bind
<222> LOCATION: (1)..(30)
<223> OTHER INFORMATION: /note="Primer LV60"

<400> SEQUENCE: 11
gtactggtac cggatccgtg aggatgttgc 30

<210> SEQ ID NO 12
<211> LENGTH: 49
<212> TYPE: DNA
<213> ORGANISM: Lelystad virus
<220> FEATURE:
<221> NAME/KEY: primer_bind
<222> LOCATION: (1)..(49)
<223> OTHER INFORMATION: /note="Primer LV83"

<400> SEQUENCE: 12
gaattcacta gttaatacga ctcactatag atgatgtgta gggtattcc 49

<210> SEQ ID NO 13
<211> LENGTH: 44
<212> TYPE: DNA
<213> ORGANISM: Lelystad virus
<220> FEATURE:
<221> NAME/KEY: primer_bind
<222> LOCATION: (1)..(44)
<223> OTHER INFORMATION: /note="Sense primer LV108"

<400> SEQUENCE: 13
ggagtggtta acctcgtcaa gtatggccgg taaaaaccag agcc 44

<210> SEQ ID NO 14
<211> LENGTH: 36
<212> TYPE: DNA
<213> ORGANISM: Lelystad virus
<220> FEATURE:
<221> NAME/KEY: primer_bind
<222> LOCATION: (1)..(36)
<223> OTHER INFORMATION: /note="Antisense primer LV112"

<400> SEQUENCE: 14
ccattcacct gactgtttaa ttaacttgca ccctga 36

<210> SEQ ID NO 15
<211> LENGTH: 36
<212> TYPE: DNA
<213> ORGANISM: Lelystad virus
<220> FEATURE:
<221> NAME/KEY: primer_bind
<222> LOCATION: (1)..(36)
<223> OTHER INFORMATION: /note="Sense primer LV111"

<400> SEQUENCE: 15
tcagggtgca agttaattaa acagtcaggt gaatgg 36

-continued

<210> SEQ ID NO 16
<211> LENGTH: 30
<212> TYPE: DNA
<213> ORGANISM: Lelystad virus
<220> FEATURE:
<221> NAME/KEY: primer_bind
<222> LOCATION: (1)..(30)
<223> OTHER INFORMATION: /note="Primer LV110"

<400> SEQUENCE: 16
cctgactgtc aatttaaatt gcaccctgac 30

<210> SEQ ID NO 17
<211> LENGTH: 30
<212> TYPE: DNA
<213> ORGANISM: Lelystad virus
<220> FEATURE:
<221> NAME/KEY: primer_bind
<222> LOCATION: (1)..(30)
<223> OTHER INFORMATION: /note="Primer LV109"

<400> SEQUENCE: 17
gtcagggtgc aatttaaatt gacagtcagg 30

<210> SEQ ID NO 18
<211> LENGTH: 10
<212> TYPE: DNA
<213> ORGANISM: Lelystad virus
<220> FEATURE:
<221> NAME/KEY: primer_bind
<222> LOCATION: (1)..(10)
<223> OTHER INFORMATION: /note="5' prime end of the genome"

<400> SEQUENCE: 18
atgatgtgta 10

<210> SEQ ID NO 19
<211> LENGTH: 37
<212> TYPE: DNA
<213> ORGANISM: Lelystad virus
<220> FEATURE:
<221> NAME/KEY: primer_bind
<222> LOCATION: (1)..(37)
<223> OTHER INFORMATION: /note="5' end"

<400> SEQUENCE: 19
taatacgact cactatagat gatgtgtagg gtattcc 37

<210> SEQ ID NO 20
<211> LENGTH: 121
<212> TYPE: DNA
<213> ORGANISM: Lelystad virus
<220> FEATURE:
<221> NAME/KEY: primer_bind
<222> LOCATION: (1)..(121)
<223> OTHER INFORMATION: /note="3'end"

<400> SEQUENCE: 20
aaaaaaaaaa aaaaaaaaaa aaaaaaaaaa aaaaaaaaaa aaaaaaaaaa aaaaaaaaaa 60
aaaaaaaaaa aaaaaaaaaa aaaaaaaaaa aaaaaaaaaa aaaaaaaaac gatcgtctag 120
a 121

<210> SEQ ID NO 21
<211> LENGTH: 6
<212> TYPE: DNA
<213> ORGANISM: Lelystad virus
<220> FEATURE:
<221> NAME/KEY: primer_bind -continued

```
<222> LOCATION: (1)..(6)
<223> OTHER INFORMATION: /note="Reverse 3' end"

<400> SEQUENCE: 21

cgatcg                                                                   6


<210> SEQ ID NO 22
<211> LENGTH: 19
<212> TYPE: RNA
<213> ORGANISM: Lelystad virus
<220> FEATURE:
<221> NAME/KEY: primer_bind
<222> LOCATION: (1)..(19)
<223> OTHER INFORMATION: /note="5' end"

<400> SEQUENCE: 22

augaugugua ggguauucc                                                    19


<210> SEQ ID NO 23
<211> LENGTH: 111
<212> TYPE: RNA
<213> ORGANISM: Lelystad virus
<220> FEATURE:
<221> NAME/KEY: primer_bind
<222> LOCATION: (1)..(111)
<223> OTHER INFORMATION: /note="3' end"

<400> SEQUENCE: 23

aaaaaaaaaa aaaaaaaaaa aaaaaaaaaa aaaaaaaaaa aaaaaaaaaa aaaaaaaaaa      60

aaaaaaaaaa aaaaaaaaaa aaaaaaaaaa aaaaaaaaaa aaaaaaaaac g               111
```

INFECTIOUS CLONES OF RNA VIRUSES AND VACCINES AND DIAGNOSTIC ASSAYS DERIVED THEREOF

CROSS-REFERENCES TO RELATED APPLICATIONS

This application is a continuation of application Ser. No. 09/874,626, which was filed Jun. 5, 2001, now abandoned, which was filed as a continuation of application Ser. No. 09/297,535 filed Oct. 12, 1999, now U.S. Pat. No. 6,268,199, which was the National Stage of International Application No. PCT/NL97/00593 filed Oct. 29, 1997.

TECHNICAL FIELD

The invention relates to the field of RNA viruses and infectious clones obtained from RNA viruses. Furthermore, the invention relates to vaccines and diagnostic assays obtainable by using and modifying such infectious clones of RNA viruses.

BACKGROUND

Recombinant DNA technology comprises extremely varied and powerful molecular biology techniques aimed at modifying nucleic acids at the DNA level and makes it possible to analyze and modify genomes at the molecular level. In this respect, viruses, because of the small size of their genome are particularly amenable to such manipulations. However, recombinant DNA technology is not immediately applicable to nonretroviral RNA viruses because these viruses do not encompass a DNA intermediate step in their replication. For such viruses, infectious clones (for instance as a DNA copy or as in vitro transcribed RNA copy or as derivative of either) have to be developed before recombinant DNA technology can be applied to their genome to generate modified virus. Infectious clones can be derived through the construction of full-length (genomic length) cDNA (here used in the broad sense of a DNA copy of RNA and not only in the strict sense of a DNA copy of mRNA) of the virus under study after which an infectious transcript is synthesized in vivo in cells transfected with the full-length cDNA, but infectious transcripts can also be obtained by in vitro transcription from in vitro ligated partial-length cDNA fragments that comprise the full viral genome. In all cases, the transcribed RNA carries all the modifications that have been introduced to the cDNA and can be used to further passage the thus modified virus.

Infectious cDNA clones and infectious in vitro transcripts have been generated for a great number of positive strand RNA viruses (for a review see Boyer and Haenni, *Virology* 198, 415-426) with a genome of up to 12 kb or slightly larger. The viral genomic length of Pestiviruses seems until now the longest positive strand viral RNA genome from which infectious clones (Moormann et al., *J. Vir.* 70:763-770) have been prepared. Problems associated with genomic length lie not only in the difficulty of obtaining and maintaining long and stabile cDNA clones in bacteria but also in the infectivity of the initial RNA transcript of which replication in the host cell has to be achieved without the help of the normally associated viral proteins connected with viral replication. To achieve successful infection, viral transcripts must interact with viral-encoded proteins, most particularly with the viral replicase and with host cell components such as the translation machinery; therefore, the structure of viral transcripts has to mimic that of virion RNA as closely as possible. Additional problems can be found with those positive strand RNA viruses that replicate via a mechanism of subgenomic messenger RNAs transcribed from the 3' side of the genome and with those positive strand RNA viruses that generate during replication defective interfering particles, such as naked capsids or empty shell particles, comprising several structural proteins but only a part of the genome. The presence of incomplete viral RNA fragments or of, for example, matrix or nucleocapsid proteins interacting or interfering with the viral RNA to be transcribed or to replicative intermediate RNA and disrupting its structure will abolish full-length RNA strand synthesis, and thus the generation of infectious virus comprising genomic length RNA.

"Lelystad virus" (LV), also called "porcine reproductive respiratory syndrome virus" (PRRSV, genomic length 15.2 kb), is a member of the family Arteriviridae, which also comprises equine arteritis virus (EAV, genomic length 12.7 kb), lactate dehydrogenase-elevating virus (LDV, genomic length at least 14.2 kb) and simian haemorrhagic fever virus (SHFV genomic length approximately 15 kb) (Meulenberg et al., 1993a; Plagemann and Moennig, 1993).

Recently, the International Committee on the Taxonomy of Viruses decided to incorporate this family in a new order of viruses, the Nidovirales, together with the Coronaviridae (genomic length 28 to 30 kb), and Toroviridae (genomic length 26 to 28 kb). Nidovirale represents enveloped RNA viruses that contain a positive-stranded RNA genome and synthesize a 3' nested set of subgenomic RNAs during replication. The subgenomic RNAs of coronaviruses and arteriviruses contain a leader sequence which is derived from the 5' end of the viral genome (Spaan et al., 1988; Plagemann and Moennig, 1993). The subgenomic RNAs of toroviruses lack a leader sequence (Snijder and Horzinek, 1993). Whereas the ORFs 1a and 1b, encoding the RNA dependent RNA polymerase, are expressed from the genomic RNA, the smaller ORFs at the 3' end of the genomes of Nidovirales encoding structural proteins are expressed from the subgenomic mRNAs.

PRRSV (Lelystad virus), or "LV", was first isolated in 1991 by Wensvoort et al. (1991). It was shown to be the causative agent of a new disease now generally known as a porcine reproductive respiratory syndrome, ("PRRS"). The main symptoms of the disease are respiratory problems in pigs and abortions in sows. Although the major outbreaks, such as observed at first in the US in 1987 and in Europe in 1991, have diminished, this virus still causes economic losses in herds in the US, Europe, and Asia.

PRRSV preferentially grows in alveolar lung macrophages (Wensvoort et al., 1991). A few cell lines, such as CL2621 and other cell lines cloned from the monkey kidney cell line MA-104 (Benfield et al., 1992; Collins et al., 1992; Kim et al., 1993), are also susceptible to the virus. Some well known PRRSV strains are known under accession numbers CNCM I-1102, I-1140, I-1387, I-1388, ECACC V93070108, or ATCC VR2332, VR2385, VR2386, VR 2429, VR 2474, and VR 2402. The genome of PRRSV was completely or partly sequenced (Conzelmann et al., 1993; Meulenberg et al., 1993a, Murthaugh et al, 1995) and encodes, besides the RNA dependent RNA polymerase (ORFs 1a and 1b), six structural proteins of which four envelope glycoproteins named $GP_2$ (ORF2), $GP_3$ (ORF3), $GP_4$ (ORF4) and $GP_5$ (ORF5), a non-glycosylated membrane protein M (ORF6) and the nucleocapsid protein N (ORF7) (Meulenberg et al. 1995, 1996; van Nieuwstadt et al., 1996). Immunological characterization and nucleotide sequencing of European and US strains of PRRSV has identified minor antigenic differences within strains of PRRSV located in the structural viral proteins (Nelson et al., 1993; Wensvoort et al., 1992; Murtaugh et al., 1995).

Pigs can be infected by PRRSV via the oronasal route. Virus in the lungs is taken up by lung alveolar macrophages and in these cells replication of PRRSV is completed within 9 hours. PRRSV travels from the lungs to the lung lymphnodes within 12 hours and to peripheral lymphnodes, bone marrow and spleen within 3 days. At these sites, only a few cells stain positive for viral antigen. The virus is present in the blood during at least 21 days and often much longer. After 7 days, antibodies to PRRSV are found in the blood. The combined presence of virus and antibody in PRRS infected pigs shows that the virus infection can persist for a long time, albeit at a low level, despite the presence of antibody. During at least 7 weeks, the population of alveolar cells in the lungs is different from normal SPF lungs.

PRRSV needs its envelope to infect pigs via the oronasal route. The normal immune response of the pig entails, among other things, the production of neutralizing antibodies directed against one or more of the envelope proteins. Such antibodies can render the virus non-infective. However, once in the alveolar macrophage, the virus also produces naked capsids, constructed of RNA encapsidated by the M and/or N protein, sometimes partly containing any one of the glycoproteins. The intra- and extracellular presence of these incomplete viral particles or (partly) naked capsids can be demonstrated by electron microscopy. Sometimes, naked capsids without a nucleic acid content can be found. The naked capsids are distributed through the body by the bloodstream and are taken up from the blood by macrophages in spleen, lymphnodes and bone marrow. These naked, but infectious, viral capsids can not be neutralized by the antibodies generated by the pig thus explaining the persistence of the viral infection in the presence of antibody. In this way, the macrophage progeny from infected bone marrow cells spreads the virus infection to new sites in the body. Because not all bone marrow macrophage-lineage cells are infected, only a small number of macrophages at peripheral sites are infected and produce virus.

PRRSV capsids, consisting of ORF7 proteins only, can be formed in the absence of other viral proteins by, for instance, infection of macrophages with a chimeric pseudorabies-ORF7 vector virus. The PRV virus was manipulated to contain ORF7 genetic information of PRRSV. After 18 hours post infection, the cytoplasm of infected cells contains large numbers of small, empty spherical structures with the size of PRRS virus nucleocapsids.

BRIEF SUMMARY OF THE INVENTION

The invention provides an infectious clone derived from a virus with a genomic length far exceeding the maximum genomic length of the positive strand RNA viruses from which infectious clones have been obtained so far. The experimental part hereof describes the generation of an infectious clone based on and derived from PRRSV with a genomic length of 15.2 kb but such clones can now also be obtained from LDV and SHFV that also have a genomic length of about 15 kb and from EAV, although its genome is slightly smaller, and from viruses with greater genomic length, such as the Coronaviridae or Toroviridae.

The invention also provides a method to generate infectious clones by circumventing the problems encountered in viral RNA strand synthesis associated with the presence of incomplete viral RNA fragments or of, for example, matrix or nucleocapsid proteins interacting or interfering with the to be transcribed RNA transcript or with replicative intermediate RNA, disrupting the structure that abolishes full-length RNA strand synthesis, and thus the generation of infectious virus.

The invention provides a method of generating infectious clones by transfecting a host cell that is, in essence, not susceptible to infection with the wild-type virus with a recombinant nucleic acid based on the genome of the virus followed by rescuing infectious progeny virus from the host cell by passaging to or cocultivation with cells that are susceptible to the virus. Cells that are, in essence, not susceptible may, in comparison with the cells that are routinely used for the replication of the virus under study, be only slightly susceptible or be not susceptible at all to the virus under study, but may be fully susceptible to other virus strains.

The invention provides a method to generate infectious clones by transfecting host cells that are not susceptible to infection with the wild-type virus, thus avoiding the generation of naked capsids or incomplete viral particles comprising RNA fragments and matrix or nucleocapsid proteins that interfere with viral RNA strand synthesis. Infectious virus is rescued from the thus transfected host cells by passaging to cells that are susceptible to the virus. In the experimental part, hereof, we describe how, in this way, an infectious clone of PRRSV is obtained, but the method is also applicable to other positive strand RNA viruses.

The invention also provides the possibility of generating a modified infectious clone via the further application of recombinant DNA technology. Such modifications may be single or multiple mutations, substitutions, deletions or insertions or combinations thereof that can be achieved via any recombinant DNA technology method known in the art. The present invention thus provides modified RNA viruses that can be used to investigate RNA viruses and to prepare vaccines.

The invention also provides infectious clones, for example, derived from Arteriviridae, such as PRRSV, which can be used as a single-purpose vaccine against the disease caused by the virus from which the infectious clone is based. For example, the infectious clone based on PRRSV can now be used to study virulence markers or serological markers of the PRRSV. Known serological markers of PRRSV are, for example, located on any of the structural proteins of PRRSV encoded by ORF2 to ORF7. They can also be found in the proteins encoded by ORF 1a and 1b.

Virulence markers are present in the ORF 1a and 1b encoding the nonstructural proteins of PRRSV but can also be found on any of the proteins encoded by ORF2 to ORF7. By modifying the genome of the infectious clone with respect to those markers, it is possible to obtain PRRSV that is not or is much less virulent than its parent strain, and/or that is modified by deleting or introducing serological markers to enable a serological differentiation between vaccinated and wild-type virus infected pigs. Such modifications are, for instance, provided by the PRRSV infectious clones in which the nucleic acid sequence encoding the ORF7 N protein is replaced by the ORF7 protein of ATCC VR2332 or LDV.

The invention also provides infectious clones, for example, derived from Arteriviridae, such as PRRSV, which can be used as a delivery system or viral vector vaccine for a wide variety of antigens. In such clones, heterologous nucleic acid sequences that do not correspond to the sequence of the virus under study are inserted. Such heterologous nucleic acid sequences can be, for example, derived from sequences encoding any antigen of choice. The antigen is a protein or peptide that can induce immunity against a pathogen. Since the virus infects macrophages and macrophage-lineage cells in bone marrow, and distributes the antigen-containing virus through its progeny cells, this viral vector vaccine infects cells central to the immune system and can present the antigens for further processing. The vector vaccine virus infects antigen presenting cells like the dendritic macrophages or the Kuppfer cells or other cells of the immune system, and can do this as an (incompletely) enveloped viral particle or as a naked capsid particle.

Since an infection with a naked capsid or an incomplete virus particle ensures a persistent infection, the immunological booster effect will cause a lifelong (because of continuous stimulation on a low level) immunity against pathogens from which the antigens are selected. The virus can be used as an antigen carrier by including in the information for epitopes of other pathogenic organisms or substances. Several of such vector vaccine viruses carrying foreign epitopic information may be mixed and administered at one time. This enables active immunity against several different antigens of one pathogen, or active immunity against several different pathogens.

The invention also provides infectious clones, for example, derived from Arteriviridae, such as PRRSV, which can be used as a dual purpose vaccine. For example, the infectious clone based on PRRSV can be used to construct a vaccine which protects against PRRSV and against another pathogen simply by combining the vector vaccine development with the development directed towards the development of a single purpose vaccine directed against PRRS. A specific dual purpose vaccine could be developed that protects against respiratory disease in pigs by inserting in the PRRS vaccine antigens derived from any of the wide variety of other respiratory pathogens that are known to infect pigs.

The invention also provides vaccines, be it single purpose, dual purpose, or vector vaccines, that are relatively safe in the sense that the vaccines cannot be shed to the environment. Safety of the vaccines (non-shedding) can be ensured by deleting the information of those viral proteins that is needed to produce enveloped, infectious virus. This virus is propagated in a cell-line that constitutively expresses the protein. Virus replicating in this complementary cell-line has a complete envelope, and is capable of infecting pig macrophages. After one replication-cycle, the progeny virus, missing the information for the envelope protein, is no longer capable of infecting other cells as an enveloped virus. Infection of macrophages in the body is still possible, as naked capsid or incomplete viral particle.

The invention also provides viral antigens and proteins that can be harvested from cell cultures infected with the modified RNA viruses according to the invention. Such antigens can be used in diagnostic assays such as ELISA's or other types of diagnostic assay known to the expert. Such assays can be used as stand-alone tests for primary diagnosis or as accompanying tests to be applied in animal populations that have been vaccinated with a discriminating or marker vaccine based on the modified RNA viruses according to the invention.

DETAILED DESCRIPTION OF THE INVENTION

Figure 1:
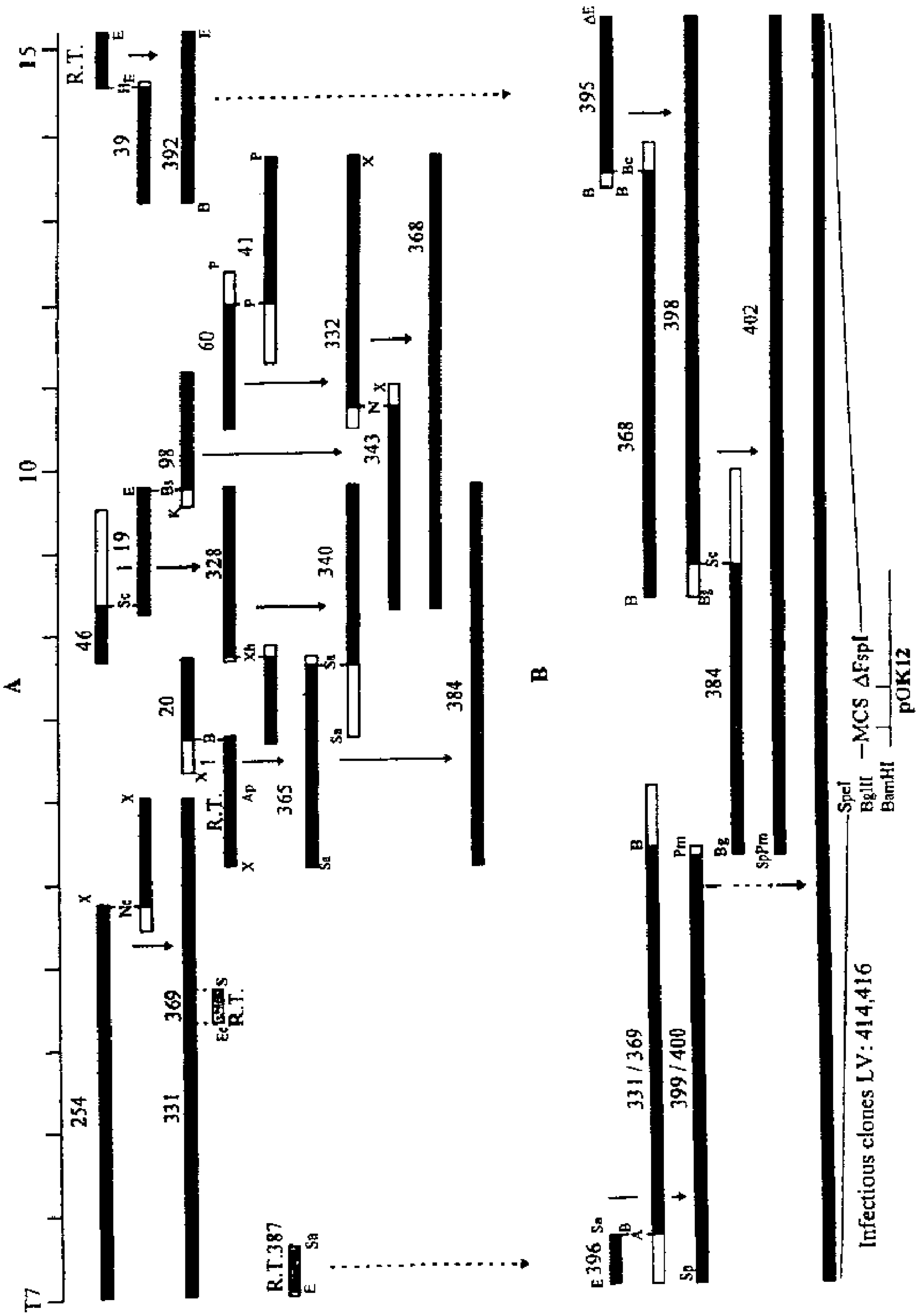
FIG. 1. Construction of a genome-length cDNA clone of LV. The upper part (A) shows the fusion of cDNA clones, which were previously sequenced (Meulenberg et al., 1993a) in pGEM4Z. The pABV numbers of the clones and the restriction sites that were used are indicated. The black boxes represent those parts of the cDNA clones that are fused in the next cloning step. Light grey boxes, indicated with R.T., are cDNA clones newly generated by RT-PCR, a dark grey box represents a new cDNA clone generated by PCR. The lower part (B) shows the assembly of the larger cDNA clones pABV331/369, pABV384, and pABV368 with the 5' end clone pABV396, containing a T7 RNA polymerase promoter, and the 3' end clone pABV395, containing a poly(A) tail, in low copy number vector pOK12. The restriction sites within and outside the multiple cloning site of pOK12 are indicated. The restriction endonuclease sites are; A, ApaI; Ap, ApoI; B, BamHI; Bg, BglII; Bs, BspE1; Bc, BclI; E, EcoRI; Ec, EcoRV; H, HindIII; K, KpnI; N, NarI; Nc, NcoI; S, SacII; Sp, SpeI; Sa, SalI; Sc, ScaI; P, PstI; Pm, PmlI; X, XbaI; Xh, XhoI.

The production of cDNA clones from which infectious RNA can be transcribed in vitro has become an essential tool for molecular genetic analysis of positive-strand RNA viruses. This technology is applicable to positive-strand RNA viruses whose RNA genomes may function as mRNA and initiate a complete infectious cycle upon introduction into appropriate host cells. For a number of viruses, infectious clones have been described that facilitate studies on the genetic expression, replication, function of viral proteins and recombination of RNA viruses (for a review, see, Boyer and Haenni, 1994). In addition, these clones can be considered for the development of new viral vectors and vaccines. An infectious cDNA clone has not been described for Arteriviruses so far. We report here the generation of an infectious clone of PRRSV and its first application in the generation of chimeric PRRSV viruses.

Cells and Viruses

The Ter Huurne strain of PRRSV (or LV) (deposited at CNCM, Paris, under accession number I-1102) was isolated in 1991 (Wensvoort et al., 1991) and was grown in primary alveolar macrophages or in CL2621 cells. Passage 6 of the Ter Huure strain (TH) was used in this study as well as a derivative of this strain, LV4.2.1, which was adapted for growth on CL2621 cells by serial passage. Alveolar macrophages were maintained in RPMI 1640 growth medium (Flow), whereas CL2621 cells were maintained in Hank's minimal essential medium (Gibco-BRL/Life technologies). BHK-21 cells were maintained in Dulbecco's minimal essential medium. For transfection experiments, BHK-21 cells were grown in Glasgow minimal essential medium (GIBCO-BRL/Life Technologies Ltd), according to the method of Liljeström and Garoff (1993).

Isolation of Viral RNAs

Intracellular RNA was isolated from alveolar macrophages or CL2621 cells 24 hours after infection with PRRSV at a multiplicity of infection of 1, as described earlier (Meulenberg et al., 1993a). In order to isolate virion genomic RNA, virions were purified on sucrose gradients as described by van Nieuwstadt et al. (1996) and were resuspended in TNE (0.01 M Tris-HCl, pH 7.2, 0.1 M NaCl, 1 mM EDTA). One ml of Proteinase K buffer (100 mM Tris-HCl, pH 7.2, 25 mM EDTA, 300 mM NaCl, 2% (w/v) SDS) and 0.4 mg Proteinase K (Boehringer Mannheim) was added to one ml of purified PRRSV virions ($10^8$ $TCID_{50}$). This reaction mixture was incubated at 37° C. for 30 min. The RNA was extracted once with phenol/chloroform (1:1) and precipitated with ethanol. The RNA was stored in ethanol at −20° C. One tenth of this RNA preparation was used in Reversed Transcription (RT) reactions.

Cloning of the 5' and 3' Termini of the PRRSV Genome.

The 5' end of the viral genome of PRRSV was cloned using a modified single strand ligation to single-stranded cDNA procedure (SLIC; Edwards et al., 1991). One tenth of the virion RNA, prepared as described above, was used in a RT reaction with primer 11U113 (5' TACAGGTGCCTGATCCAAGA 3') (SEQ ID NO: 1) which is complementary to nucleotides 1232 to 1251 of the genome. The RT reaction was performed in a final volume of 20 ml, as described earlier (Meulenberg et al., 1993b). Subsequently, 2 ml 6M NaOH was added to the RT-reaction and the RNA was hydrolyzed for 30 min at 37° C. The single strand cDNA was purified using the high pure PCR Product Purification Kit of Boehringer Mannheim. The purified cDNA was precipitated with ethanol, resuspended in TE, and ligated to an anchor primer ALG3 (5'CACGAATTCACTATCGATTCTGGATCCTTC 3') (SEQ ID NO: 2). This primer contains an EcoRI, ClaI, and BamHI site, and its 3' end is modified with an amino blocking group to prevent self-ligation. The single strand cDNA product was ligated to 4 pmol ALG3 in 50 mM Tris-HCl (pH 8.0), 10 mM $MgCl_2$, 10 mg/ml BSA, 25% PEG, 1.0 mM Hexamine Cobaltchloride, 40 mM ATP, and 0.5 ml (10 U) T4 RNA ligase (New England Biolabs), overnight at room temperature. One third of the ligation reaction was used as template in a PCR with primers LV69 (5' AGGTCGTCGACGGGCCCCGTGATCGGGTACC 3') (SEQ ID NO: 3) and ALG4 (5' GAAGGATCCAGAATCGATAG 3') (SEQ ID NO: 4). Primer LV69 is complementary to nucleotides 594 to 615 of the LV genome, whereas ALG4 is complementary to anchor primer ALG3. The PCR conditions were as described in Meulenberg et al. (1993b) and the obtained product was digested with EcoRI and SalI and cloned in pGEM-4Z. A similar strategy was used to clone the 5' terminus of the LV genome from intracellular LV RNA. For these experiments 10 mg of total cellular RNA isolated from CL2621 cells infected with LV was used. The 5' cDNA clones were sequenced and one clone, pABV387, containing an extension of 10 nucleotides compared to the published PRRSV sequence (Meulenberg et al., 1993a), was used for further experiments.

A 3' end cDNA clone containing a long poly(A) tail was constructed by reverse transcription of LV RNA with primer LV76 (5' TCTAGGAATTCTAGACGATCG$(T)_{40}$ 3') (SEQ ID NO: 5), which contains an EcoRI, XbaI, and PvuI site. The reversed transcription reaction was followed by a PCR with primers LV75 (5' TCTAGGAATTCTAGACGATCGT 3') (SEQ ID NO: 6), which is identical to LV76 except for the poly(T) stretch, and 39U70R (5' GGAGTGGTTAACCTCGTCAA 3') (SEQ ID NO: 7), a sense primer corresponding to nucleotides 14566-14585 of the LV genome and containing a HpaI site. The resulting PCR products were digested with HpaI and EcoRI and cloned in cDNA clone pABV39 restricted with the same enzymes (FIG. 1). Two cDNA clones containing a poly(A) stretch of 45 A's (pABV382) and 109 A's (pABV392) and the correct genomic cDNA sequence, as assessed by oligonucleotide sequencing, were used to construct the full length genomic cDNA clone.

Sequence Analysis.

Oligonucleotide sequences were determined with the PRISM™ Ready Reaction Dye Deoxy™ Terminator Cycle Sequencing Kit and Automatic sequencer of Applied Biosystems.

Construction of Full-Length Genomic cDNA Clones of PRRSV.

cDNA clones generated earlier to determine the nucleotide sequence of the genome of LV (Meulenberg et al., 1993a), were ligated together at convenient restriction sites as shown in FIG. 1. Plasmid pABV254 was constructed from pABV clones 25, 11, 12, and 100 and was used in a previous study (den Boon et al., 1996). Standard cloning procedures were carried out according to Sambrook et al. (1989). This resulted in three plasmids containing overlapping cDNA sequences of LV in high copy number plasmid pGEM4Z. Plasmids pABV331 and pABV369 consist of nucleotides 5 to 6015 of the LV genome. A nucleotide difference was found at position 3462 at a ratio of 1:1 in a set of 6 independent cDNA clones which were sequenced in that region. This nucleotide difference resulted in an amino acid substitution at position 1084 in ORF1A (Leu instead of Pro). Since we could not predict the influence of this amino acid on infectivity, we also cloned the Leu encoding cDNA fragment in pABV331 by exchange at the EcoRV (nucleotide 3403) and SacII (nucleotide 3605) site, which resulted in pABV369. Plasmid pABV384 consists of nucleotides 5168 to 9825 of the LV genome. Since no appropriate cDNA clone was yet available that had overlap with plasmids pABV20 and pABV5, and could finally be fused to the cDNA sequences of pABV331 and pABV369, two new cDNA fragments were generated by RT-PCR. Sense primer LV59 (5' TCGGAATCTAGATCTCACGTGGTGCAGCTGCTG 3') (SEQ ID NO: 8) corresponding to nucleotides 5169-5186 and antisense primer 61U303 (5' CATCAACACCTGTGCAGACC 3') (SEQ ID NO: 9) complementary to nucleotides 6078 to 6097 were used in one PCR. Sense primer 61U526R (5' TTCCTTCTCTGGCGCATGAT 3') (SEQ ID NO: 10) located at nucleotides 5936 to 5955 and LV60 (5' GTACTGGTACCGGATCCGTGAGGATGTTGC 3') (SEQ ID NO: 11) complementary to nucleotides 6727 to 6745 were used in another PCR. These two PCR fragments were ligated together in pABV20 using the XbaI site incorporated in LV59, the internal ApoI site (nucleotides 6006) and the BamHI site at nucleotide 6740, which was also incorporated in primer LV60. The new cDNA fragment was completely sequenced and did not contain any mutations that resulted in amino acid differences with the published sequence (Meulenberg et al., 1993a). Plasmid pABV368 encompasses nucleotides 8274 to 13720 of the PRRSV genome. Since further ligation of cDNA fragments in pGEM-4Z resulted in instable clones, the inserts of pABV331/369, pABV384, and pABV368 were ligated to the 5' and 3' cDNA fragments in pOK12 (Viera and Messing, 1991). Plasmid vector pOK12 is expected to be more suitable for cloning of large foreign cDNA sequences, because it has a lower copy number than pGEM-4Z. Plasmids were transformed to *Escherichia coli* strain DH5a, grown at 32° C. in the presence of 15 mg/ml Kanamycin, to keep the copy number as low as possible. First, the cDNA fragments of pABV382 ($(A)_{45}$) and pABV392 ($(A)_{109}$) were excised by digestion with EcoRI and modification of this site with Klenow polymerase (Pharmacia) to a blunt end, followed by digestion with BamHI. These fragments were cloned in pOK12 digested with BamHI and FspI, the latter site also modified to a blunt end, resulting in pABV394 and pABV395. In this way, the T7 RNA polymerase promoter present in pOK12 was removed. Subsequently, the cDNA fragments of pABV368 and pABV384 were ligated to the 3' end cDNA clones using the BclI site (nucleotide 13394), the ScaI site (nucleotide 8657) and the BamHI and BglII sites in flanking or vector sequences. This resulted in plasmids pABV401 and pABV402 (FIG. 1).

A 5' cDNA clone, containing the T7 RNA polymerase promoter directly fused to the 5' terminus of the LV genome, was amplified by PCR from pABV387 with primers LV83 (5' GAATTCACTAGTTAATACGACTCAC-TATAGATGATGTGTAGGGTATTCC 3') (SEQ ID NO: 12) and LV69. LV83 is composed of, in order from 5' to 3', an EcoRI and SpeI site, a T7 RNA polymerase promoter sequence, a single G for initiation of transcription, and nucleotides 1 to 19 of the LV genome. The PCR fragment was cloned in the EcoRI and SalI site of pOK12, resulting in pABV396. The correct sequence of pABV396 was assessed by oligonucleotide sequencing. Subsequently, the LV cDNA fragments of pABV331 and pABV369 were excised with ApaI and BamHI, and were ligated to pABV396, digested with ApaI and BamHI. Finally, the resulting 5' cDNA fragments were cloned into pABV401 and pABV402, using the SpeI site upstream of the T7 RNA polymerase promoter and the unique PmlI site at position 5168 in the viral genome. In this way, genome-length cDNA clones were obtained as corresponding to viruses resembling the parent strain and to chimeric viruses comprising foreign open reading frames.

Production of Mutant Viruses Containing a PacI and/or SwaI Site

To introduce a unique PacI site in the genome-length cDNA clone directly downstream of the ORF7 gene, the T and A at nucleotides 14987 and 14988 were both replaced by an A in a PCR using sense primer LV108 (5' GGAGTGGT-TAACCTCGTCAAGTATGGCCGG-TAAAAACCAGAGCC3') (SEQ ID NO: 13) with antisense primer LV 112 (5'CCATTCACCTGACTGTTTAATTAACT-TGCACCCTGA3') (SEQ ID NO: 14) and sense primer LV111 (5'TCAGGGTGCAAGTTAATTAAACAGTCAG-GTGAATGG 3') (SEQ ID NO: 15) with LV75. Similarly, a unique SwaI site was created by changing the G at position 14980 for a T, and the T at position 14985 for an A by PCR with primers LV108 and LV110 (5'CCTGACTGTCAATT-TAAATTGCACCCTGAC 3') (SEQ ID NO: 16) and primers LV109 (5'GTCAGGGTGCAATTTAAATTGACAGTCAGG 3') (SEQ ID NO: 17) and LV111. The PCR fragments were ligated in pABV395 using the created PacI and SwaI site and flanking HpaI and XbaI sites, resulting in pABV427 and pABV426, respectively. This fragment was then inserted in pABV414 using the same unique HpaI and XbaI sites, resulting in pABV437 and pABV442 (see, FIG. 4). To detect the marker mutation in the virus recovered from transcripts of pABV437 and pABV422, RNA was isolated from the supernatant of infected porcine alveolar macrophages. This RNA was used in reverse transcription-PCR to amplify a fragment approximately 0.6 kb (spanning nucleotides 14576-polyA tail of variable length) with primers LV76, LV75 and 39U70R. The presence of the genetic marker was detected by digesting the PCR fragments with PacI or SwaI.

In Vitro Transcription and Transfection of RNA

Plasmids pABV414, pABV416, containing the full-length genomic cDNA fragment of LV, were linearized with PvuI, which is located directly downstream of the poly(A) stretch. Plasmid pABV296, which consists of ORF4 in Semliki Forest virus (SFV) expression vector pSFV1 (Meulenberg et al., 1997), was linearized with SpeI and served as control for in vitro transcription and transfection experiments. The linearized plasmids were precipitated with ethanol and 1.5 mg of these plasmids was used for in vitro transcription with T7 RNA polymerase (plasmids pABV414, pABV416) or Sp6 RNA polymerase (pABV296), according to the methods described for SFV by Liljeström and Garoff (1991 and 1993). The in vitro transcribed RNA was precipitated with isopropanol, washed with 70% ethanol and stored at −20° C. until use. BHK-21 cells were seeded in M6 wells (approximately $10^6$ cells/well) and transfected with 2.5 mg RNA mixed with 10 ml lipofectin in optimem as described by Liljeström and Garoff (1993). Alternatively, RNA was introduced in BHK-21 cells by electroporation. In this case, 10 mg in vitro transcribed RNA or 10 mg intracellular LV RNA was transfected to approximately $10^7$ BHK-21 cells using the electroporation conditions of Liljeström and Garoff (16). The medium was harvested 24 hours after transfection and transferred to CL2621 cells to rescue infectious virus. Transfected and infected cells were tested for expression of LV-specific proteins by an immuno peroxidase monolayer assay (IPMA), essentially as described by Wensvoort et al. (1986). Monoclonal antibodies (MAbs) 122.13, 122.59, 122.9 and 122.17, directed against the $GP_3$, $GP_4$, M and N protein (van Nieuwstadt et al., 1996) were used for staining in the IPMA.

Reconstruction of the 5' Terminal Sequence of the Genomic RNA of LV.

Although the infectivity of in vitro-transcribed RNAs with truncated 5' ends have been reported (Davis et al. 1989, Klump et al., 1990), it is generally admitted that the entire viral sequence, including the utmost 5' and 3' end, are required to obtain infectious clones. To clone the 5' end of the LV genome, a modified single strand ligation to single-stranded cDNA (SLIC; Edwards et al., 1991) procedure was used. Both intracellular RNA isolated from CL2621 cells infected with LV and LV RNA from purified virions was reverse transcribed using primer LV69, which was complementary to the 5' end of ORF1A. The first strand cDNA product was ligated to an anchor primer ALG3 of which the 3' end was blocked for self ligation. The ligated products were amplified by PCR and cloned. Twelve clones, derived from LV intracellular RNA and resulting from two independent PCRs, and fourteen clones derived from virion RNA and resulting from two independent PCRs were sequenced. From these 26 cDNA clones, 22 clones contained an extension of 10 nucleotides (5' ATGATGTGTA 3') (SEQ ID NO: 18) compared to the cDNA sequence, published previously (Meulenberg et al., 1993a), whereas four clones lacked one to three nucleotides at the 5' end of this additional sequence (Table 1). This led us to conclude that these ten nucleotides represent the utmost 5' end of the LV genome and were therefore incorporated in the genome-length cDNA clone.

Construction of Genome-Length cDNA Clones of LV

In order to construct a genome-length cDNA clone of LV, cDNAs that were isolated and sequenced previously (Meulenberg et al., 1993a) were joined at shared restriction enzyme sites, according to the strategy depicted in FIG. 1. In addition, new cDNA fragments were generated to assemble the genome-length cDNA clones. One cDNA fragment spanning nucleotides 5168 to 6740 was created by RT-PCR to enable the ligation of cDNA sequences from clones pABV5 and pABV20. A T7 RNA polymerase promoter for in vitro transcription was directly linked to the 5' terminus of the genome of LV by PCR and this new cDNA fragment, cloned in pABV396, and was inserted in the genome-length cDNA clone. Resequencing of nucleotides 3420 to 3725 on six new and independent cDNA clones indicated that at amino acid 1084 in ORF1a a Leu and Pro are present at a ratio of 1:1. Since we could not predict the influence of this amino acid on the infectivity of the RNA transcribed from the final genome-length cDNA clone, we used both to construct this clone. At the 3' end, two different cDNA clones were used. We had previously isolated 3' end cDNA clones containing poly(A) tails of at maximum 20 A's (Meulenberg et al., 1993a). However, in view of studies reported on the length of poly(A) tails of related viruses such as LDV (Chen et al., 1994), the entire poly(A) tail was expected to be much longer. Therefore, new 3' end cDNA clones were generated using primer LV76 which contains a stretch of 40 T residues. These cDNA clones were sequenced and contained stretches of 40 to 109 A residues. The cDNA clone containing the longest poly(A) stretch (109 A residues; pABV392) was used for the genome-length cDNA clone. Since long homo-polymeric tracts might interfere with the replication of plasmids in *E. coli* (Deng and Wu, 1981), we also selected a second clone, pABV382, containing 45 A residues for use in subsequent cloning steps. Previously, it was observed that maintenance of genome-length cDNA clones in high copy number plasmids leads to accumulation of mutations or deletions which results in loss of infectivity of transcripts synthesized from these clones (Lai et al, 1991; Rice et al., 1987; Sumiyoshi et al., 1992). We also observed instability of plasmids, when we tried to ligate the larger cDNA fragments of pABV clones 331/369, 384, and 368 to the 5' and 3' end in pGEM-4Z and, therefore, we finally fused these clones to each other in low copy number vector pOK12 (Viera and Messing, 1991). This resulted in the genome-length cDNA clones pABV414/415 and 416, which could be stably propagated in *E. coli* under the growth conditions used. No difference in stability of the genome-length cDNA clones containing 45 or 109 A residues was observed.

Infectivity of LV RNA

LV, preferentially, grows in porcine alveolar macrophages. Thus far, cell line CL2621 or other clones derived from the monkey kidney cell line MA104, are cell lines which have been shown to propagate LV (Benfield et al., 1992; Collins et al., 1992; Kim et al., 1993). Therefore, CL2621 cells were used to determine the optimal conditions for transfection of LV RNA.

RNA isolated from CL2621 cells infected with LV was transfected to CL2621 cells at different doses using different methods, such as lipofectin, lipofectamin, DEAE-dextran and electroporation. Cells were screened for cythopathic effect and plaques until 7 days post transfection, but these signs of infectious virus could not be detected. In addition, no LV-specific antigens could be detected in IPMA using LV-specific MAbs. RNA transcribed in vitro from pABV296 was used as control in these experiments. Plasmid pABV296 consists of the ORF4 gene encoding $GP_4$ inserted in expression vector pSFV1 (Meulenberg et al., 1997).

The transfection efficiency of the pABV296 RNA was tested by staining of the transfected cells in IPMA with $GP_4$-specific MAbs. The highest transfection efficiency, resulting in 0.01% positive CL2621 cells, was obtained by electroporation, whereas 80-90% positive cells were obtained using similar conditions with BHK-21 cells.

These results indicated that CL2621 cells were not suitable for transfection experiments, whereas the BHK-21 cells (not susceptible to infection with wild-type virus) surprisingly appeared very suitable. Therefore BHK-21 cells were used to test the infectivity of LV RNA. Two mg of RNA isolated from CL2621 cells infected with LV was transfected to approximately $10^6$ BHK-21 cells with lipofectin, according to the conditions described for SFV (Liljeström and Garoff, 1993).

Twenty-four hours after transfection, cells were stained with LV-specific MAb 122.17 directed against the N protein of LV. Approximately 3-10 individual cells were stained positive, but no infectious centers or plaques suggesting cell to cell spread were observed. Transfection of the control RNA transcribed from pABV296 resulted in 60-70% positive BHK-21 cells using these conditions. The supernatant of the BHK-21 cells transfected with intracellular LV RNA and pABV296 RNA were transferred to CL2621 cells.

After 3 to 4 days, plaques were observed in the cells that were incubated with the supernatant from BHK-21 cells transfected with intracellular LV RNA, but not in those incubated with supernatant from BHK-21 cells transfected with pABV296 RNA. The plaques were positively stained with LV-specific MAbs in IPMA. Similar results were obtained when RNA isolated from purified virions of LV was used. Furthermore, the number of positively stained cells increased 2 to 4 fold when cells were transfected by electroporation.

These data indicated that LV can not infect BHK-21 cells because, most likely, they lack the receptor for LV. However, once the genomic RNA has been introduced in BHK-21 cells, new infectious virus particles are being produced and excreted into the medium. Reinfection of already transfected BHK-21 cells with these particles being naked capsids or fully or partly enveloped particles is again not possible.

In Vitro Synthesis of Infectious RNA.

Figure 2:
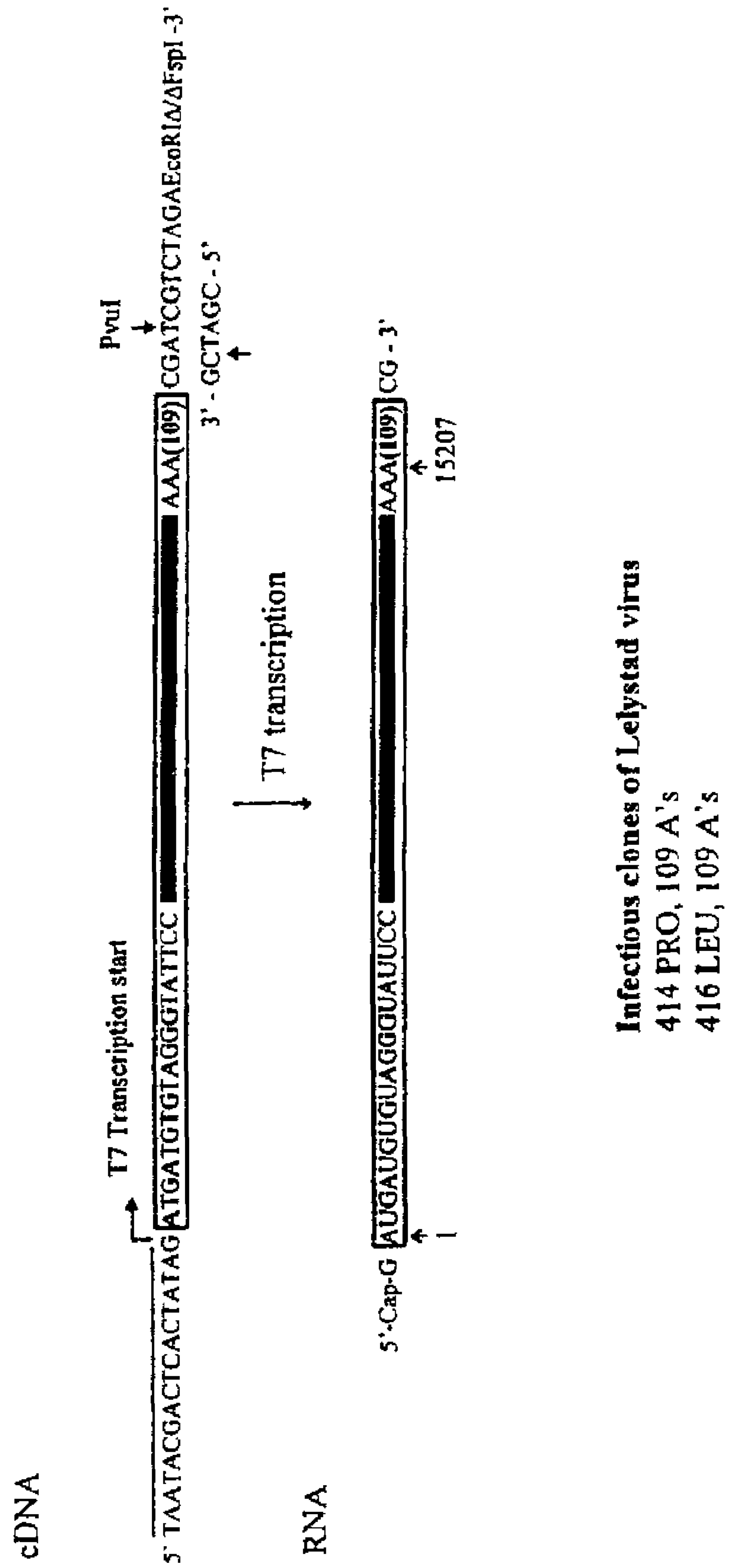
FIG. 2. Terminal sequences of cloned full-length LV cDNA and infectious RNA transcribed from this cDNA clone. Genome-length cDNA clones were linearized with PvuI and were transcribed in the presence of the synthetic cap analog $m^7G(5')ppp(5')G$ with T7 RNA polymerase. The resulting RNA should contain one extra nucleotide (G) at the 5' end and two extra nucleotides (GC) at the 3' end. The arrows in the RNA correspond to the 5' and 3' terminal nucleotides corresponding to the authentic LV RNA sequence.

Since the—to a wild-type PRRSV in essence not susceptible—BHK-21 cells were specifically appropriate for the rescue of virus from intracellular LV RNA and the susceptible CL2621 cells were not, BHK-21 cells were used to test whether RNA transcribed from the genome-length cDNA clones was infectious. Plasmids pABV414/416 were linearized with PvuI and transcribed in vitro using T7 RNA polymerase. The PvuI site is located directly downstream of the poly(A) stretch, such that the transcribed RNA contains 2 non-viral nucleotides at the 3' end (FIG. 2). In addition, transcripts should contain a non-viral G at the 5' end, which is the transcription start site of T7 RNA polymerase. Approximately 2.5 mg of in vitro transcribed RNA was transfected to BHK-21 cells, together with 2 mg intracellular LV RNA as a positive control for subsequent virus rescue in CL2621 cells, and pABV296 RNA as a positive control for RNA transfection to BHK-21 cells and negative control for subsequent virus rescue in CL2621 cells. At 24 hours after transfection, the supernatant of the cells was harvested and the cells were fixed and stained in IPMA with N-specific MAb 122.17. Whereas only a few positive cells were observed in the wells with BHK-21 cells that were transfected with intracellular LV RNA, 800 to 2700 positive cells were observed in the wells with BHK-21 cells transfected with RNA transcribed from pABV414/416. In order to check whether infectious virus was released from the cells, the supernatants were used to infect CL2621 cells. Plaques were produced in CL2621 cultures that were infected with the supernatant from BHK-21 cells transfected with intracellular LV RNA and transcripts of pABV414/415. The plaques stained positive in IPMA with MAbs against the N, M, $GP_4$, and $GP_3$ protein, suggesting that these proteins were all properly expressed. No plaques and staining in IPMA was observed in CL2621 cultures incubated with the supernatant of BHK-21 cells transfected with RNA transcribed from pABV296. Therefore, these results clearly show that transfection of RNA transcribed from genome-length cDNA clones pABV414 and pABV416 to BHK-21 cells results in the production and release of infectious LV. Moreover, when transcripts of pABV414 and pABV416 were transfected to BHK-21 cells by electroporation instead of lipofectin, a two- to four fold increase of cells staining positive with LV-specific MAbs was obtained. The titer of the recombinant viruses in the supernatant of these electroporated BHK-21 cells was approximately $10^5$ $TCID_{50}$/ml.

Growth Curves of Infectious Copy Virus Compared to Ter Huurne and LV4.2.1:

Growth Characteristics of Rescued Virus

Figure 3:
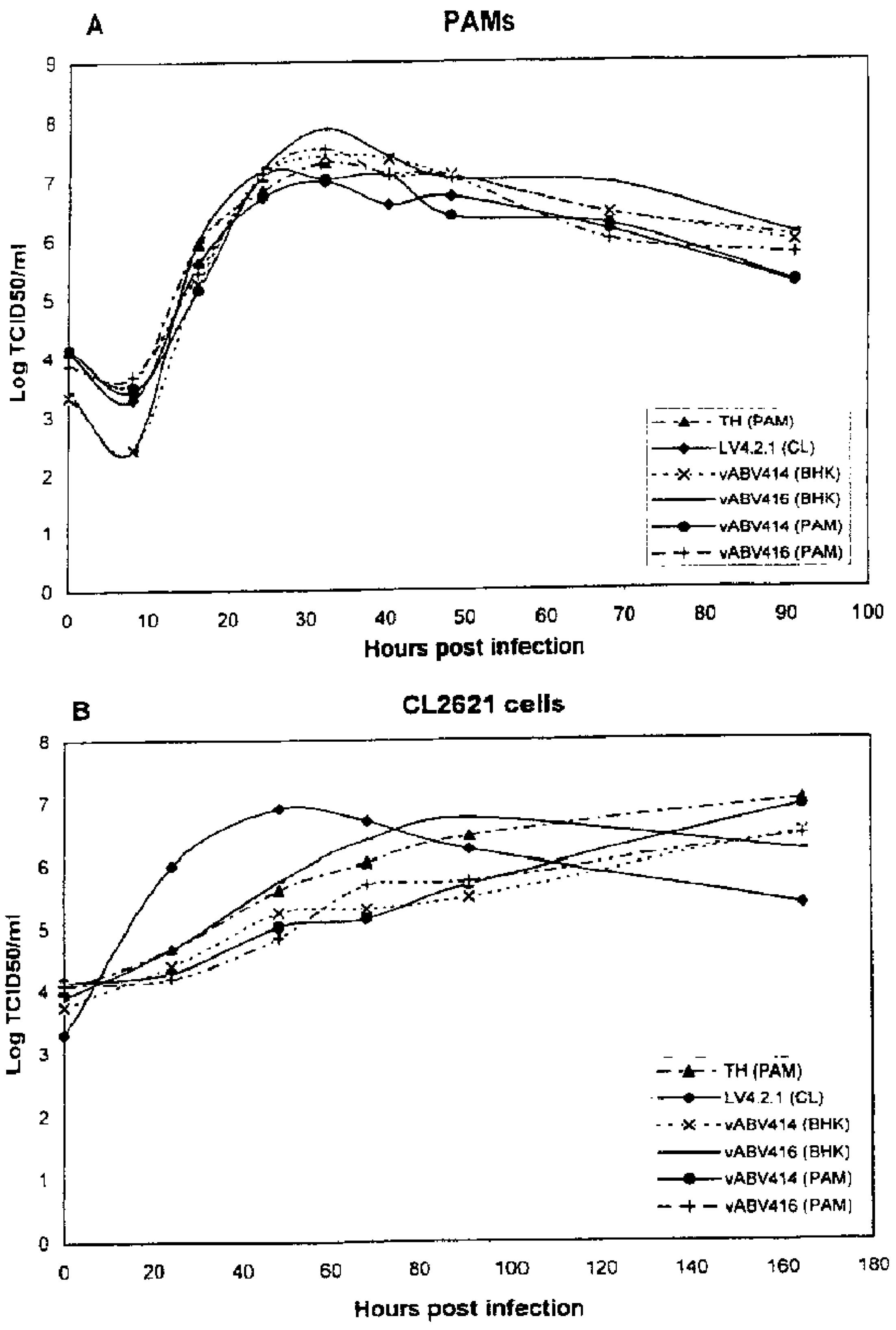
FIG. 3. Growth curves of LV wild-type virus TH, LV4.2.1, and recombinant viruses vABV414 and vABV416 in porcine alveolar macrophages (A) and CL2621 cells (B). The recombinant viruses vABV414 and vABV416 produced in BHK-21 cells were either used directly (BHK), or used after multiplication in Porcine alveolar macrophages (PAM). The TH virus was prepared in porcine alveolar macrophages (PAM), whereas LV4.2.1 was prepared in CL2621 cells (CL). The cell cultures were infected with the indicated viruses at an MOI of 0.05 and harvested at the indicated time points. Virus titers ($TCID_{50}$/ml) were determined on Porcine alveolar macrophages or CL2621 cells by endpoint dilution.

The initial transfection and infection experiments suggested that the rescued recombinant viruses, designated vABV414 and vABV416, infect and grow equally well in porcine alveolar macrophages, but grow slower on CL2621 cells than the virus rescued from BHK-21 cells transfected with intracellular LV RNA. This intracellular LV RNA was isolated from CL2621 cells infected with LV4.2.1, which has been adapted for growth on CL2621. To study the growth properties of vABV414 and vABV416 more thoroughly, growth curves were determined in CL2621 cells and porcine alveolar macrophages and were compared with those of wild-type LV that has only been passaged on porcine alveolar macrophages (TH) and with those of LV4.2.1 grown on CL2621 cells. The growth rates of the two recombinant viruses did not differ, growing equally well regardless of whether they were derived directly from BHK-21 or further passaged on porcine alveolar macrophages (FIG. 3). Titers (7.1-7.9 $TCID_{50}$/ml) in porcine alveolar macrophages peaked around 32 hours post infection, whereas the titers in CL2621 where slower and had not yet peaked even at 96 hours post infection. TH virus had growth characteristics similar to the recombinants. In contrast, the CL2621-adapted virus LV4.2.1 grew faster on CL2621 cells than the viruses vABV414, vABV416 and TH (FIG. 3). In summary, these results demonstrate that the growth properties of the recombinant viruses are similar to those of the TH virus. This was expected, since the cDNA sequence used to construct the infectious clones was derived from the parental "non-adapted" TH virus.

Introduction of a Genetic Marker in the Infectious Clone of LV

Figure 4:
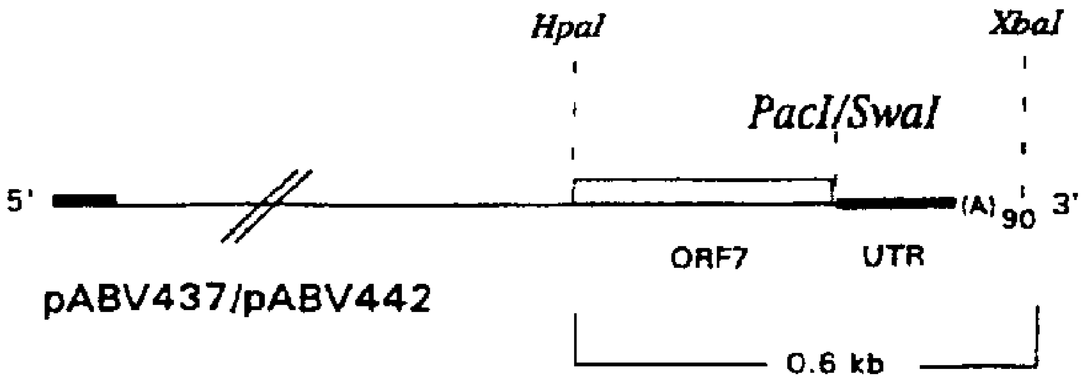
FIG. 4. Introduction of a unique PacI and SwaI site in the infectious cDNA clone of LV. The PacI and SwaI sites were created by PCR-directed mutagenesis, as described in detail in Materials and Methods. The cDNA fragments containing the PacI and SwaI site were exchanged in pABV414 using its unique HpaI and XbaI sites, which are indicated. This resulted in pABV437 and pABV442, respectively.

To demonstrate that the genome-length cDNA clone can be used to generate mutant LV viruses, a unique PacI and SwaI site was introduced directly downstream of the ORF7 gene by PCR-directed mutagenesis (FIG. 4). When RNA transcribed from the genome-length cDNA clone pABV437 containing the PacI site and pABV442 containing the SwaI site was transfected to BHK-21 cells and the supernatant was transferred to porcine alveolar macrophages and CL2621 cells at 24 hours after transfection, infectious virus was produced. The rescued viruses, vABV437 and vABV442, had similar growth properties in porcine alveolar macrophages and CL2621 cells as the parental virus vABV414 (data not shown). A specific region of approximately 0.6 kb (nucleotides 14576-poly(A) tail) was amplified by reverse transcription and PCR of viral RNA isolated from the supernatant of porcine alveolar macrophages infected with vABV414 and vABV416. Digestion with PacI showed that this restriction site was indeed present in the fragment derived from vABV437 but was absent from the fragment derived from vABV414. Similarly, the presence of SwaI site in vABV442 was demonstrated (data not shown). Thus we were able to exclude the possibility of contamination with wild-type virus and therefore we confirmed the identity of vABV437 and vABV442.

BEST MODE

Modern recombinant DNA technology allows us to analyze and modify genomes at the molecular level and thus gain deeper insight into their organization and expression. In the case of RNA viruses, this requires the generation of genome-length cDNA clones from which infectious transcripts can be synthesized. In most instances, a prerequisite for the construction of infectious clones is the identification of the sequences at the termini of the respective viral genome which are probably crucial for replication of viral RNA. In a previous study, it was shown that LV contains a poly(A)tail at the 3' end (Meulenberg et al., 1993a). In the present work, the exact 5' end of the LV genome was determined. Whereas several methods have been described to determine the 5' end of viral genomic RNAs or mRNAs, but most of them have important limitations. For flaviruses and pestiviruses, a method has been used which is based on the circularization of genomic RNA. However, this method needs accompanying analyses to define the border between the 5' and 3' end of the genome. The 5' rapid amplification of cDNA ends (5' RACE) method is based on the addition of a homopolymeric tail with terminal deoxyribonucleotide transferase (TdT) to the first strand cDNA strand. However, the tailing reaction is rather inefficient and this method also requires additional analyses since it can not be concluded whether the first nucleotide of the tail represents the viral sequence or is already part of the enzymatically added tail. As described above, we have determined the utmost 5' end of the viral genome by ligation of an oligonucleotide with a specified sequence to a first strand primer extension product and amplification by PCR. An extension of 10 nucleotides (ATGATGTGTA) (SEQ ID NO: 19) with respect to the published sequence was found in several independent clones and were therefore assumed to represent the utmost 5' end nucleotides of the viral genome. Altogether, this results in a leader sequence of 221 nucleotides, which is similar in length to the leader of EAV (207 nucleotides; den Boon et al., 1991), SHFV (208 nucleotides; Zeng et al., 1995), but longer than the leader of LDV (155 nucleotides; Chen et al., 1994). However, no significant homology exists between the leader sequences of these arteriviruses.

The utmost 5' end was incorporated in genome-length cDNA to create an infectious clone. Major problems with the generation of infectious clones concern the stability of the virus sequences when cloned in bacteria as well as the generation of the correct 5' and 3' termini. Although initial attempts to assemble a genome-length cDNA clone in pGEM4Z failed, the methods and principles of the present invention produced the 15,207 nucleotides long genomic cDNA fragment of LV which remained stable in low copy number plasmid pOK12. As noted above this cDNA fragment is now the longest infectious clone of a positive RNA strand virus thus far generated. Transcripts of the genomic-length cDNA clones contained a 5' cap structure and an extra non-viral G at the 5' end and a nonviral CG at the 3' end, but these extensions did not abolish their infectivity. Several investigators have reported a reduced initial infection of RNA transcribed from full-length cDNA clones due to extraneous, non-authentic sequences at either the 5' or 3' ends or to incomplete capping. Transcripts of LV full-length cDNA lacking a cap structure were not infectious. Whereas the infectivity of transcripts of infectious cDNA clones have always been tested in cell lines that are susceptible to the virus, we were unable to demonstrate the infectivity of transcripts from genome-length cDNA clones or LV RNA isolated from CL2621 cells by transfection of these RNAs to CL2621 cells.

This was due to the poor transfection efficiency in CL2621 cells, whereby viral RNA strand synthesis is probably hampered by interference or interaction with incomplete RNA fragments or capsid proteins resulting from reinfection of the CL2621 cells with defective interfering particles such as naked capsids containing only fragments of the viral genome. However, transfection of transcripts from full-length cDNA clones and intracellular LV RNA to BHK-21 resulted in the production and release of infectious virus which could be rescued in CL2621 cells. Reinfection of BHK-21 cells with naked capsids does not occur and thus does not hamper full-length viral RNA synthesis. The specific infectivity was roughly 400-1500 positive cells per mg in vitro transcribed RNA, whereas 2 to 5 positive cells were obtained per mg LV intracellular RNA. However, these specific infectivities can not be compared because only a very small fraction of the intracellular RNA isolated from LV-infected CL2621 cells represent genomic LV RNA. Furthermore, the amount of genomic RNA isolated from virions which was used for transfections was too small to allow accurate quantification.

In addition, BHK-21 cells were scored for antigen production in IPMA with LV-specific MAbs, which does not necessarily correlate with production of infectious virus. This was clear from the fact that the supernatant of BHK-21 cells transfected with 2 mg intracellular LV RNA contained a higher titer of plaque forming units assayed on CL2621 cells than the supernatant of BHK-21 cells transfected with 2.5 mg transcript of full-length cDNA clones. Although it was shown previously for a number of viruses that the length of the poly(A) tail influenced the infectivity of the viral transcripts (Holy and Abouhaidar, 1993; Sarow, 1989), we did not observe any difference in infectivity between transcripts from genomic cDNA clones containing a tail of 45 or 109 residues. It might be possible that a tail of 45 A residues is above a threshold length below which stability of the corresponding transcripts will be altered. We have found a clone difference at amino acid 1084 in ORF1a, giving a PRO and LEU at a ratio of 1:1. This amino acid did not have an influence on infectivity since transcripts of full-length cDNA clones containing this LEU or PRO codon did not display any difference in infectivity of BHK-21 cells.

The genome-length infectious clone was used to generate a chimeric virus expressing the nucleocapsid protein of PRRSV strain ATCC VR2332. In addition, the genome-length infectious clone was used to generate a chimeric virus expressing the nucleocapsid protein of the mouse virus LDV. The chimeric viruses can be distinguished from parental viruses with strain-specific MAbs. They do not stain with monoclonal antibodies specifically reactive with the N (ORF7) protein of the Ter Huurne strain of PRRSV. Furthermore, the chimeric virus in which the PRRSV N protein is substituted with the LDV N protein is not reactive with porcine convalescent antibodies reactive with the PRRSV N protein. Since all PRRSV infected pigs develop antibodies directed against the PRRSV N protein, the chimeric viruses can be used for future projects using new live vaccines against PRRSV, making use of this virus as a vector system which is specifically targeted to its host cell, the alveolar lung macrophage. In this respect, it should be mentioned that initial attempts to confer protection with killed virus or recombinant subunits were disappointing. The up-to-date, only effective, vaccine against PRRS available is a modified live vaccine based on a US strain (Gorcyca, et al., 1995). However, pigs vaccinated with this modified live product can not be discriminated from pigs infected with field virus. The infectious clone of PRRSV thus provides a so-called marker vaccine by site-directed mutagenesis of the genome, such that vaccinated pigs can be distinguished from field virus-infected pigs on the basis of difference in serum antibodies. A distinguishing assay can thus be fashioned using methods known to those skilled in the art.

The infectious clone of LV, described here, is the longest infectious clone ever developed of a positive strand RNA virus and the first of the arterivirus family. The generation of this infectious clone of PRRSV opens up new opportunities for studies directed at the pathogenesis, host tropism, and replication and transcription of this virus. Arteriviruses and coronaviruses share a specific transcription mechanism also referred to as leader primed transcription which involves the generation of a so-called nested set of subgenomic RNAs containing a common 5' leader (Spaan et. al., 1988; Plagemann and Moennig, 1991). This leader primed transcription is a complex process which is not yet fully understood. Studies of coronavirus virologist to elucidate the underlying mechanism of leader-primed transcription are restricted to analyses and site directed mutagenesis of cDNAs of defecting interfering RNAs, since the large size of the genome (28 to 30 kb) has impeded the construction of an infectious clone. The infectious clone of PRRSV thus provides a model system to study and unravel the intriguing mechanism of transcription and replication of arteriviruses and coronaviruses.

Infectious clones derived from PRRSV can also be used as a delivery system or vector vaccine virus for foreign antigens inserted in the PRRSV genome because the virus infects macrophages and macrophage-lineage cells in bone marrow and other cells of the immune system and distribute the antigen-containing virus through its progeny cells. In the specific instance of antigens containing fragments of the ORF7 or N protein of Arteriviruses or PRRSV, these antigens will be (ove)expressed at the outer side of the cell membrane of the infected cell, thereby further enhancing the immune response. Such immunological booster effects will cause a lifelong (because of continuous stimulation on a low level) immunity against pathogens. We can use the virus as an antigen carrier by building in the information for epitopes of other pathogenic organisms or substances. Several modified PRRS viruses carrying foreign epitopic information may be mixed and administered at one time. This enables active immunity against several different epitopes of one pathogen, or active immunity against several different pathogens. Safety of the modified PRRSV vaccines (such as non-shedding) can be ensured by deleting the information of those viral proteins that are needed to produce enveloped, infectious virus. This virus has to be propagated in a cell-line that constitutively expresses that envelope protein. Virus replicating in this complementary cell-line has a complete envelope and is capable of infecting macrophages in the pig. After one replication-cycle, the progeny virus, missing the information for the envelope protein, is no longer capable of infecting other cells as a fully enveloped virus. Infection of macrophages in the body is still possible as naked capsid. In this way, the vaccine will be contained to the animal that has been vaccinated and will not spread to other animals.

REFERENCES

Benfield, D. A., E. Nelson, E. Collins, J. E., Harris, L., Goyal, S. M., Robison, D., Christianson, W. T., Morrison, R. B., Gorcyca, D. E., and Chladek, D. W. (1992). Characterization of swine infertility and respiratory syndrome virus (Isolate ATCC-VR2332) *J. Vet. Diagn. Invest.* 4, 127-133.

Boyer, J., and Haenni, A. (1994) Infectious transcripts and cDNA clones of RNA viruses. *Virology,* 198, 415-426.

Chen, Z., Faaberg, K. S., and Plagemann, P. G. W. (1994) Determination of the 5' end of the lactate dehydrogenase-elevating virus genome by two independent approaches. *J. Gen. Virol.* 75, 925-930.

Collins, J. E., Benfield, D. A., Christianson, W. T., Harris, L., Hennings, J. C., Shaw, D. P., Goyal, S. M., McCullough, S., Morrison, R. B., Joo, H. S., Gorcyca, D. E., Chladek, D. W. (1992). Isolation of swine infertility and respiratory syndrome virus (Isolate ATCC-VR-2332) in North America and experimental reproduction of the disease in gnotobiotic pigs. *J. of Vet. Diagn. Invest.* 4, 117-126.

Conzelmann, K. K., Visser, N., van Woensel, P., and Tiel, H. J. (1993). Molecular characterization of porcine reproductive and respiratory syndrome virus, a member of the Arterivirus group. *Virology* 193, 329-339.

den Boon, J. A., Faaberg, K. S., Meulenberg, J. J. M., Wassenaar, A. L. M., Plagemann, P. G. W., Gorbalenya, A. E., and Snijder, E. J. (1995) Processing and evolution of the N-terminal region of the arterivirus replicase ORF1a protein: identification of two papainlike cysteine proteases. *J. Virol.* 69: 4500-4505.

Davis, N. L., Willis, L. V., Smith, J. F., and Johnston, R. E. (1989). In vitro synthesis of infectious Venezuelan equine encephalitis virus RNA of an insect virus. *Proc. Natl. Acad. Sci.* USA 83, 63-66.

Deng, R., and Wu, R. (1981). An improved procedure for utilizing terminal transferase to add homopolymers to the 3' termini of DNA. *Nucleic Acids Res.* 9, 4173-4188.

Edwards, J. B. D. M., Delort, J., and Mallet, J. (1991) Oligodeoxyribonucleotide ligation to single-stranded cDNAs; A new tool for cloning 5' ends of mRNAs and for contructing cDNA libraries by in vitro amplification. *Nucleic Acids Res.* 19, 5227-5232.

Gorcyca, D., Schlesinger, K., Chladek, D., et al., (1995) *Proc. Am. Assoc. of Swine Pract.*, Ohama, Nebr., 1-22.

Holy, S., and Abouhaidar, M. G. (1993). Production of infectious in vitro transcripts from a full-length clover yellow mosaic virus cDNA clone. *J. Gen. Virol.*, 74, 781-784.

Kim, H. S., Kwang, J., and Yoon, I. Y. (1993). Enhanced replication of porcine reproductive and respiratory syndrome virus in a homogeneous subpopulation of MA-104 cell line. *Arch. Virol.* 133, 477-483.

Klump, W. M., Bergmann, I., Muller, B. C., Ameis, D., and Kandolf, R. (1990) Complete nucleotide sequence of infectious coxsackie-virus B3 cDNA: Two initial 5'uridine residues are regained during plus-strand RNA synthesis. *J. Virol.* 64, 1573-1583.

Lai, C. J., Zhao, B., Hori, H., and Bray, M. (1991) Infectious RNA transcribed from stably cloned full-length cDNA of dengue type 4 virus. *Proc. Natl. Acad. Sci.* USA 88, 5139-5143.

Liljeström, P. and Garoff, H. (1991). A new generation of animal cell expression vectors based on the Semliki Forest virus replicon. *Biotechnol.* 9, 1356-1361.

Liljeström, P., and Garoff, H. (1993) Expression of proteins using Semliki Forest virus vectors, p. 16.xx.1-16.xx.00 In: Current protocols in Molecular Biology, F. M. Ausubel, R. Brent, R. E. Kingston, D. D. Moore, J. A. Smith, J. G. Seidman and K. Struhl (Eds.). Greene Publishing associates and Wiley interscience, New York.

Meulenberg, J. J. M., Hulst, M. M., de Meijer, E. J., Moonen, P. L. J. M., den Besten, A., de Kluyver, E. P., Wensvoort, G., and Moormann, R. J. M. (1993a). Lelystad virus, the causative agent of porcine epidemic abortion and respiratory syndrome (PEARS) is related to LDV and EAV. *Virology* 192, 62-74.

Meulenberg, J. J. M., de Meijer, E. J., and Moormann, R. J. M. (1993b). Subgenomic RNAs of Lelystad virus contain a conserved junction sequence. *J. of Gen. Virol.* 74, 1697-1701.

Meulenberg, J. J. M., Petersen-den Besten, A., de Kluyver, E. P., Moormann, R. J. M., Wensvoort, G (1995). Characterization of proteins encoded by ORFs 2 to 7 of Lelystad virus. *Virology* 206, 155-163.

Meulenberg, J. J. M., and Petersen-den Besten (1996) Identification and characterization of a sixth structural protein of Lelystad virus: The glycoprotein $GP_2$ encoded by ORF2 is incorporated in virus particles. *Virology*, in press.

Meulenberg et al., 1997

Murtaugh, M. P., Elam, M. R, and Kakach (1995) Comparison of the structural protein coding sequences of the VR-2332 and Lelystad virus strains of the PRRS virus. *Arch. Virol.*, 140, 1451-1460.

Nelson, E. A., Christopher-Hennings, J., Drew, T., Wensvoort, G., Collins, J. E., and Benfield, D. A. (1993). Differentiation of United states and European isolates of porcine reproductive and respiratory syndrome virus by monoclonal antibodies. *J. of Clin. Microbiol.* 31, 3184-3189.

Plagemann, P. G. W., and Moennig, V. (1991). Lactate dehydrogenase-elevating virus, equine arteritis virus, and simian hemorrhagic fever virus: a new group of positive-strand RNA viruses. *Adv. in Virus Res.* 41, 99-192.

Rice, C. M., Levis, R., Strauss, J. H., and Huang, H. V. (1987). Production of infectiuos RNA transcripts from Sindbis virus cDNA clones: mapping of lethal mutations, rescue of a temperature-sensitive marker, and in vitro mutagenesis to generate defined mutants. *J. Virol.*, 61, 3809-3819.

Sambrook, J., Fritsch, E. F., and Maniatis, T. (1989). Molecular Cloning, A Laboratory Manual. Cold Spring Harbor Lab., Cold Spring Harbor, N.Y.

Sarnow, P. (1989) Role of 3' end sequences in infectivity of polio-virus transcripts made in vitro. *J. Virol.*, 63, 467-470.

Snijder, E. J., and Horzinek, M. C. (1993). Toroviruses: replication, evolution and comparison with other members of the coronavirus-like superfamily. *J, Gen. Virol.*, 74, 2305-2316.

Spaan, W. J. M., Cavanagh, D., and Horzinek, M. C. (1988) Coronaviruses: Structure and genome expression. *J. Gen. Virol.* 69, 2939-2952.

Sumiyoshi, H., Hoke, C. H., and Trent, D. W. (1992). Infectious Japanese encephalitis virus RNA can be synthesized from in vitro-ligated cDNA templates. *J. Virol.*, 66, 5425-5431.

van Nieuwstadt, A. P., Meulenberg, J. J. M., van Essen-Zandbergen, A., Petersen-den Besten, A., Bende, R. J., Moormann, R. J. M., and Wensvoort, G. (1996). Proteins encoded by ORFs 3 and 4 of the genome of Lelystad virus (Arteriviridae) are structural proteins of the virion. *J. Virol.*, 70, 4767-4772.

Viera, J., and Messing, J. (1991) New pUC-derived cloning vectors with different selectable markers and DNA replication origins. *Gene*, 100, 189-194.

Wensvoort, G., de Kluyver, E. P., Luijtze, E. A., de Besten, A., Harris, L., Collins, J. E., Christianson, W. T., and Chladek, D. (1992) Antigenic comparison of Lelystad virus and swine infertility ans respiratory (SIRS) virus. *J. Vet. Diagn. Invest.* 4, 134-138.

Wensvoort, G., Terpstra, C., Boonstra, J., Bloemraad, M., and Van Zaane, D. (1986) Production of monoclonal antibodies against swine fever virus and their use in laboratory diagnosis. *Vet. Microbiol.* 12, 101-108.

Wensvoort, G., Terpstra, C., Pol, J. M. A., Ter Laak, E. A., Bloemraad, M., de Kluyver, E. P., Kragten, C., van Buiten, L., den Besten, A., Wagenaar, F., Broekhuijsen, J. M., Moonen, P. L. J. M., Zetstra, T., de Boer, E. A., Tibben, H. J., de Jong, M. F., van 't Veld, P., Groenland, G. J. R., van Gennep, J. A., Voets, M. Th., Verheijden, J. H. M., and Braamskamp, J. (1991). Mystery swine disease in the Netherlands: the isolation of Lelystad virus. Vet. Quart. 13, 121-130.

Zeng, L., Godeny, E. K., Methven, S. L., and Brinton, M. A. (1995) Analysis of simian hemorrhagic fever virus (SHFV) subgenomic RNAs, junction sequences and 5' leader. Virology 207, 543-548.

TABLE 1

Nucleotide sequence of 5' end clones of LV.

| Sequence 1 | No. of clones |
|---|---|
| ATGATGTGTAGGG..... | 22 |
| TGATGTGTAGGG..... | 1 |
| GATGTGTAGGG..... | 2 |
| ATGTGTAGGG..... | 1 |

1) The underlined nucleotides represent additional sequences that were not found in cDNA clones isolated and sequenced previously (Meulenberg et al., 1993a).

What is claimed is:

1. A method of generating an infectious clone based upon the genome of a porcine reproductive respiratory syndrome virus (PRSSV) RNA, said method comprising: producing a recombinant nucleic acid comprising at least one full-length DNA copy or in vitro-transcribed RNA copy transfecting a host cell that is not susceptible to infection by that virus wherein said host cell is a BHK-21 cell and isolating infectious virus clones from the transfected host cell by cocultivation of the transfected host cell with cells that are susceptible to infection by said virus and rescuing infectious clones from said co-cultivated host cells.

2. A method of generating an infectious clone based upon an RNA virus's genome, said method comprising: producing a recombinant nucleic acid comprising at least one full-length DNA copy or in vitro-transcribed RNA copy and selecting infectious clones by transfecting a host cell with said recombinant nucleic acid wherein said host cell is a BHK-21 cell, wherein the virus is PRRSV.

* * * * *

UNITED STATES PATENT AND TRADEMARK OFFICE

CERTIFICATE OF CORRECTION

PATENT NO. : 8,546,124 B2
APPLICATION NO. : 11/239529
DATED : October 1, 2013
INVENTOR(S) : Meulenberg et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 984 days.

Signed and Sealed this
Fourth Day of August, 2015

Michelle K. Lee

Michelle K. Lee
*Director of the United States Patent and Trademark Office*